United States Patent
Matsumoto et al.

(10) Patent No.: US 11,070,739 B2
(45) Date of Patent: Jul. 20, 2021

(54) ENDOSCOPE SYSTEM HAVING A FIRST LIGHT SOURCE FOR IMAGING A SUBJECT AT DIFFERENT DEPTHS AND A SECOND LIGHT SOURCE HAVING A WIDE BAND VISIBLE BAND

(71) Applicant: OLYMPUS CORPORATION, Tokyo (JP)

(72) Inventors: Koji Matsumoto, Tokyo (JP); Sho Shinji, Tokyo (JP); Kenji Urushibata, Tokyo (JP); Hiroyuki Kubo, Tokyo (JP); Tetsuhiro Oka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/691,961

(22) Filed: Nov. 22, 2019

(65) Prior Publication Data
US 2020/0099845 A1    Mar. 26, 2020

Related U.S. Application Data

(63) Continuation of application No. PCT/JP2017/021664, filed on Jun. 12, 2017.

(51) Int. Cl.
*H04N 7/18*     (2006.01)
*H04N 5/235*    (2006.01)
(Continued)

(52) U.S. Cl.
CPC .......... *H04N 5/2354* (2013.01); *A61B 1/045* (2013.01); *A61B 1/0638* (2013.01)

(58) Field of Classification Search
CPC .... H04N 5/2354; H04N 5/2256; A61B 1/045; A61B 1/0638; A61B 1/00096; A61B 1/00009; G01B 11/2518
(Continued)

(56) References Cited

U.S. PATENT DOCUMENTS 6,464,633 B1    10/2002   Hosoda et al.
7,519,096 B2 *   4/2009   Bouma ............... A61B 5/0066
                                                    372/102
(Continued)

FOREIGN PATENT DOCUMENTS

EP     2229870 A1     9/2010
EP     2520214 A1    11/2012
(Continued)

OTHER PUBLICATIONS

International Search Report dated Aug. 22, 2017 issued in PCT/JP2017/021661.
(Continued)

*Primary Examiner* — Shan E Elahi
(74) *Attorney, Agent, or Firm* — Scully, Scott, Murphy & Presser, P.C.

(57) ABSTRACT

An endoscope system of the present invention includes: a first illumination unit that emits first illumination light for imaging two sets of image information about a subject at different depths; a second illumination unit that emits second illumination light having a wide band covering a visible band from a position different from the position of the first illumination light; an imaging unit that images a first illumination image and a second illumination image of the subject that is illuminated with the first illumination light and the second illumination light; a separation processing unit that separates the two sets of image information from the first illumination image; and a separated-image generating unit that generates two separated images by processing the second illumination image using the two sets of image information.

12 Claims, 18 Drawing Sheets

(51) Int. Cl.
*A61B 1/045* (2006.01)
*A61B 1/06* (2006.01)

(58) Field of Classification Search
USPC .......................................................... 348/68
See application file for complete search history.

(56) References Cited

U.S. PATENT DOCUMENTS

| | | | |
|---|---|---|---|
| 2001/0055462 A1* | 12/2001 | Seibel ................ | A61B 1/00172 385/147 |
| 2002/0165456 A1 | 11/2002 | Canpolat et al. | |
| 2010/0048995 A1 | 2/2010 | Suijver et al. | |
| 2010/0056928 A1* | 3/2010 | Zuzak .................. | A61B 5/0071 600/476 |
| 2010/0195078 A1 | 8/2010 | Horiuchi et al. | |
| 2010/0240953 A1 | 9/2010 | Murakami | |
| 2010/0245551 A1 | 9/2010 | Morita | |
| 2011/0263955 A1 | 10/2011 | Narita et al. | |
| 2012/0123205 A1* | 5/2012 | Nie ...................... | A61N 5/0075 600/109 |
| 2012/0302847 A1 | 11/2012 | Ozawa et al. | |
| 2012/0327205 A1 | 12/2012 | Takahashi | |
| 2013/0270421 A1 | 10/2013 | Kanamori et al. | |
| 2014/0052005 A1 | 2/2014 | Yokota | |
| 2014/0092227 A1 | 4/2014 | Kanamori et al. | |
| 2014/0267657 A1 | 9/2014 | Takei et al. | |
| 2015/0022647 A1 | 1/2015 | Takei et al. | |
| 2015/0238089 A1* | 8/2015 | Fujinuma ........... | A61B 1/00071 600/473 |
| 2015/0320296 A1* | 11/2015 | Morita .................. | G06T 7/0012 348/65 |
| 2016/0041334 A1 | 2/2016 | Suijver et al. | |
| 2016/0278678 A1 | 9/2016 | Valdes et al. | |
| 2016/0334340 A1 | 11/2016 | Ollivier et al. | |
| 2017/0006202 A1 | 1/2017 | Otani et al. | |
| 2017/0098301 A1 | 4/2017 | Ikemoto et al. | |
| 2017/0231480 A1 | 8/2017 | Yamazaki | |
| 2018/0164221 A1* | 6/2018 | Singh .................... | G01N 21/76 |
| 2020/0099844 A1 | 3/2020 | Shinji et al. | |
| 2020/0100650 A1 | 4/2020 | Oka | |
| 2020/0100660 A1 | 4/2020 | Matsumoto et al. | |

FOREIGN PATENT DOCUMENTS

| | | | | |
|---|---|---|---|---|
| EP | 2526854 A1 | 11/2012 | | |
| EP | 2979607 A1 | 2/2016 | | |
| EP | 3075301 A1 | 10/2016 | | |
| EP | 3202306 A1 | 8/2017 | | |
| JP | 2009-536066 A | 10/2009 | | |
| JP | 2010-213992 A | 9/2010 | | |
| JP | 2010-227256 A | 10/2010 | | |
| JP | 2012-239816 A | 12/2012 | | |
| JP | 2014-18439 A | 2/2014 | | |
| JP | 2014-188222 A | 10/2014 | | |
| JP | 2015-077415 A | 4/2015 | | |
| JP | 2015-231498 A | 12/2015 | | |
| JP | 2016-49370 A | 4/2016 | | |
| JP | 2016-174836 | 10/2016 | | |
| JP | 2016-198304 A | 12/2016 | | |
| JP | 2016-200418 A | 12/2016 | | |
| JP | 2016-209466 A | 12/2016 | | |
| JP | 2017-042629 A | 3/2017 | | |
| WO | WO 2007/132378 A2 | 11/2007 | | |
| WO | WO 2011/080996 A1 | 7/2011 | | |
| WO | WO 2011/081141 A1 | 7/2011 | | |
| WO | WO-2011081141 A1 * | 7/2011 | ........... | A61B 1/0638 |
| WO | WO 2015/016013 A1 | 2/2015 | | |
| WO | WO 2016/151903 A1 | 9/2016 | | |
| WO | 2016/181720 A1 | 11/2016 | | |
| WO | WO 2018/229831 A1 | 12/2018 | | |
| WO | WO 2018/229833 A1 | 12/2018 | | |
| WO | WO 2018/229834 A1 | 12/2018 | | |

OTHER PUBLICATIONS

International Search Report dated Aug. 15, 2017 issued in PCT/JP2017/021664.
International Search Report dated Aug. 22, 2017 issued in PCT/JP2017/021665.
International Search Report dated Aug. 22, 2017 issued in PCT/JP2017/021667.
Shree K. Nayar et al., "Fast separation of direct and global components of a scene using high frequency illumination", ACM Transactions on Graphics (Jul. 3, 2006), vol. 25, Issue 3, pp. 935-944, cited in ISR.
T. Takatani et al., "Decomposition of Reflected and Scattered Lights by Multiple Weighted Measurements", 14th Symposium on Image Recognition and Understanding (MIRU2011) (Jul. 2011).
K. Tanaka et al., "Adaptive Frequency Selection under Parallel High-frequency Illumination", 16th Symposium on Image Recognition and Understanding (MIRU2013), Collection of Extended Abstract, Information Processing Society of Japan, Yoshiki Shimotsuma, SS2-33, cited in ISR.
T. Takatani et al., "Decomposition of Reflected and Scattered Lights by Multiple Weighted Measurements", IPSJ SIG Technical Report (CD-ROM), vol. 2011, No. 1, ROMBUNNO.CVIM-177, No. 12, ISSN 2186-2583, cited in ISR.
Office Action dated Jun. 19, 2020 received in U.S. Appl. No. 16/691,865.
International Search Report dated Jul. 24, 2018 issued in International Application No. PCT/JP2018/021590, together with partial English machine translation.
International Search Report dated Jul. 24, 2018 issued in International Application No. PCT/JP2018/021597, together with partial English machine translation.
Office Action dated Dec. 3, 2020 received in U.S. Appl. No. 16/702,964, 13 pages.

* cited by examiner

| D/L | SURFACE-LAYER IMAGE | DEEP-LAYER IMAGE |
|---|---|---|
| 0 |  |  |
| 0.023 |  |  |
| 0.045 |  |  |
| 0.068 |  |  |
| 0.113 |  |  |

ENDOSCOPE SYSTEM HAVING A FIRST LIGHT SOURCE FOR IMAGING A SUBJECT AT DIFFERENT DEPTHS AND A SECOND LIGHT SOURCE HAVING A WIDE BAND VISIBLE BAND

CROSS-REFERENCE TO RELATED APPLICATIONS

This is a continuation of International Application PCT/JP2017/021664, with an international filing date of Jun. 12, 2017, which is hereby incorporated by reference herein in its entirety.

TECHNICAL FIELD

The present invention relates to endoscope systems.

BACKGROUND ART

Light produced by an illuminated object contains a plurality of types of components, such as specular reflection light, diffuse reflection light, and scattered light. A proposed technique separates these components contained in an object image using a high-frequency pattern projection method, which uses structured illumination light having a stripe light/dark pattern, to separate information about the surface of the object and information about the inside of the object (for example, see Non-Patent Literature 1).

A technique for measuring the shape of an object also uses structured illumination light (for example, see Patent Literatures 1 and 2). Structured illumination light is generated by utilizing interference of light in Patent Literature 1, and structured illumination light is generated by projecting a grid pattern formed on a substrate in Patent Literature 2.

CITATION LIST

Non-Patent Literature

{Non-Patent Literature 1} Tsuyoshi TAKATANI et al., "Decomposition of Reflected and Scattered Lights by Multiple Weighted Measurements", The 14th Meeting on Image Recognition and Understanding (MIRU2011), July, 2011

Patent Literature

{PTL 1} Japanese Unexamined Patent Application Publication No. 2016-200418
{PTL 2} Japanese Unexamined Patent Application Publication No. 2016-198304

SUMMARY OF INVENTION

An aspect of the present invention is an endoscope system including: a first illumination unit that emits, from a first exit face to a subject, first illumination light for imaging two sets of image information about the subject at different depths; a second illumination unit that emits, from a second exit face disposed at a different position from the first exit face to the subject, second illumination light having a wide band covering a visible band; an imaging unit that images a first illumination image of the subject illuminated with the first illumination light, and a second illumination image of the subject illuminated with the second illumination light; a separation processing unit that separates the two sets of image information from the first illumination image; and a separated-image generating unit that processes the second illumination image using the two sets of image information to generate two separated images each containing a large amount of information about the subject at the different depths.

DESCRIPTION OF EMBODIMENTS

An endoscope system 1 according to an embodiment of the present invention will be described below with reference to the drawings.

Figure 1:
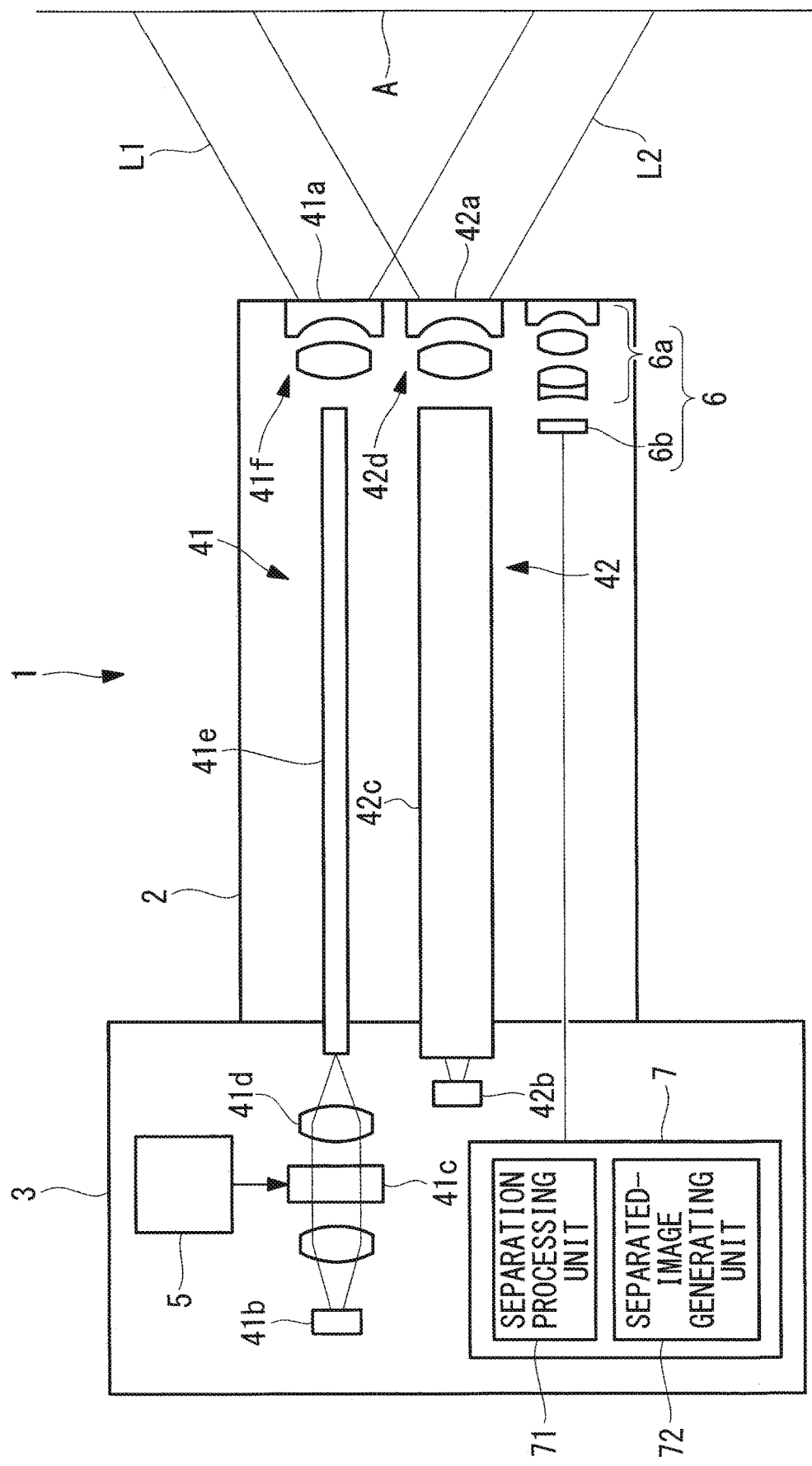
FIG. 1 shows the overall configuration of an endoscope system according to an embodiment of the present invention.

As shown in FIG. 1, the endoscope system 1 according to this embodiment includes an endoscope 2 for observing the inside of the body, and a body part 3 connected to the base end of the endoscope 2.

The endoscope system 1 also includes a first illumination unit 41 and a second illumination unit 42 that emit illumination light L1 and L2 from the distal end of the endoscope 2 toward biological tissue (subject) A inside the body, an intensity-distribution changing unit 5 that changes the intensity distribution of the first illumination light L1 with time, an imaging unit 6 that images first and second illumination images of the biological tissue A illuminated with the illumination light L1 and L2, and an image processing unit 7 that processes the first and second illumination images imaged by the imaging unit 6 to generate two separated images having information at different depths in the biological tissue A.

The first illumination unit 41 has a first exit face 41a provided at the distal end face of the endoscope 2 and emits, from the first exit face 41a to the biological tissue A, white first illumination light L1 having a spatially non-uniform intensity distribution in a beam cross-section perpendicular to the optical axis. Typically, the first illumination light L1 has such an intensity gradient that the brightness gradually decreases from the center of the beam toward the periphery. Besides this overall intensity gradient at the beam cross-section, the first illumination light L1 has, at the beam cross-section, a structured light/dark pattern, in which high-intensity light portions and dark portions, which have lower intensity than the light portions or have no intensity, are alternately repeated.

This first illumination unit 41 includes a light source 41b provided in the body part 3, a mask 41c, a light-collecting lens 41d, and, provided in the endoscope 2, an image guide fiber 41e and a projection lens 41f.

The light source 41b is a semiconductor light source, using, for example, an LED or an LD. Alternatively, the light source 41b may be an exit end of an optical fiber connected to a light source device (not shown) outside the body part 3.

The mask 41c is a liquid-crystal element whose light transmittance at respective positions in an incident area, on which white light is incident, can be electrically controlled, and a projection pattern including light-transmission areas, which allow the white light to pass therethrough, and light-blocking areas, which block the white light, and corresponding to the light/dark pattern is formed thereon. The white light output from the light source 41b is provided with a light/dark pattern as it passes through the mask 41c and becomes the first illumination light L1. The thus-generated first illumination light L1 is focused at the entrance end of the image guide fiber 41e by the light-collecting lens 41d because the size of the starting point at the subject-side distal end portion of the endoscope 2 needs to be reduced. The first illumination light L1 is then guided to the projection lens 41f provided at the distal end of the endoscope 2 through the image guide fiber 41e while preserving the light/dark pattern and is emitted as a divergent beam from the first exit face 41a, which is the distal end face of the projection lens 41f, by the projection lens 41f.

The second illumination light L2 is wideband white light having a spectrum covering substantially the entire visible band. The second illumination unit 42 has a second exit face 42a provided at the distal end face of the endoscope 2 and emits, from the second exit face 42a to the biological tissue A, white second illumination light L2 having a spatially substantially uniform intensity distribution in a beam cross-section perpendicular to the optical axis. The second exit face 42a is disposed beside the first exit face 41a. This second illumination unit 42 includes a light source 42b provided in the body part 3, and a bundle fiber 42c and a projection lens 42d provided in the endoscope 2.

The light source 42b is a semiconductor light source using, for example, an LED or an LD or a lamp light source, such as a xenon lamp. The white light may be generated by mixing red, green, and blue light output from a plurality of light sources 42b. The white light output from the light source 42b is guided to the projection lens 42d, provided at the distal end of the endoscope 2, through the bundle fiber 42c and is emitted as a divergent beam from the second exit face 42a, which is the distal end face of the projection lens 42d, by the projection lens 42d.

The first illumination unit 41 and the second illumination unit 42 are controlled by a control unit (not shown) provided in the body part 3 so as to alternately emit the first illumination light L1 and the second illumination light L2 toward the biological tissue A.

The intensity-distribution changing unit 5 is a control device for controlling the light transmittance at the respective positions in the incident area of the mask 41c and changes, with time, the intensity distribution of the first illumination light L1 such that the light portions and the dark portions are switched at the beam cross-section. This allows the light portions and the dark portions to be alternately projected, in order, at the respective positions in the irradiation area of the first illumination light L1 on the surface B of the biological tissue A.

FIGS. 2A to 2F each show an example light/dark pattern of the intensity distribution of the first illumination light L1 and the temporal change thereof. In FIGS. 2A to 2F, the white areas show the light portions, and the black areas show the dark portions.

Figure 2A:
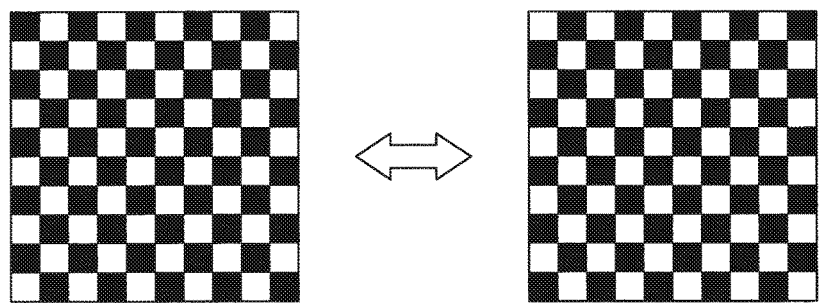
FIG. 2A shows an example intensity distribution of first illumination light and the temporal change thereof.

The light/dark pattern in FIG. 2A is a checkered pattern in which square light portions and dark portions are alternately repeated in two directions perpendicular to each other.

Figure 2B:
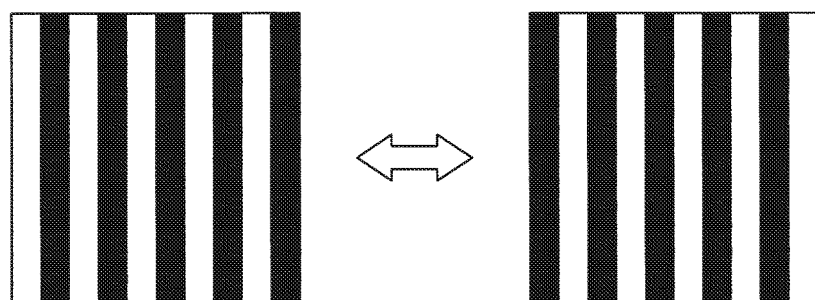
FIG. 2B shows another example intensity distribution of the first illumination light and the temporal change thereof.
Figure 2C:
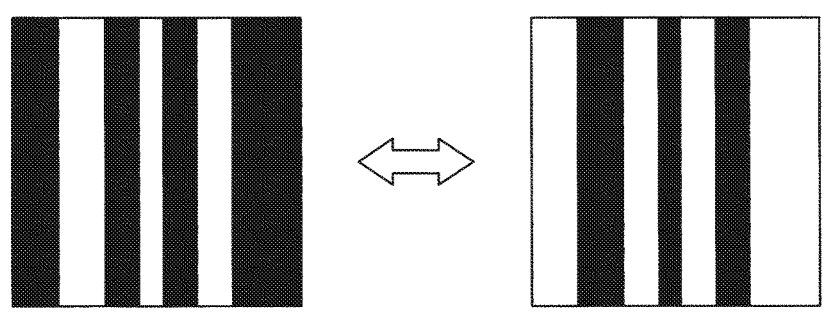
FIG. 2C shows another example intensity distribution of the first illumination light and the temporal change thereof.

The light/dark patterns in FIGS. 2B and 2C are stripe patterns in which linear band-like light portions and dark portions are alternately repeated only in the width direction, which is perpendicular to the longitudinal direction of the light portions and the dark portions. In the stripe patterns, the spatial period of the light portions and the dark portions may be either regular, as shown in FIG. 2B, or irregular, as shown in FIG. 2C.

Figure 2D:
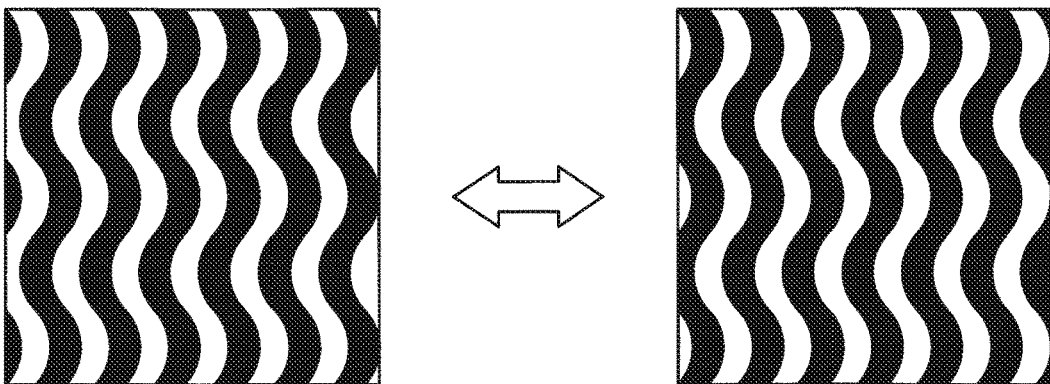
FIG. 2D shows another example intensity distribution of the first illumination light and the temporal change thereof.

The light/dark pattern in FIG. 2D is a stripe pattern in which wave-like band-like light portions and dark portions are alternately repeated only in the width direction, which is perpendicular to the longitudinal direction of the light portions and the dark portions.

Figure 2E:
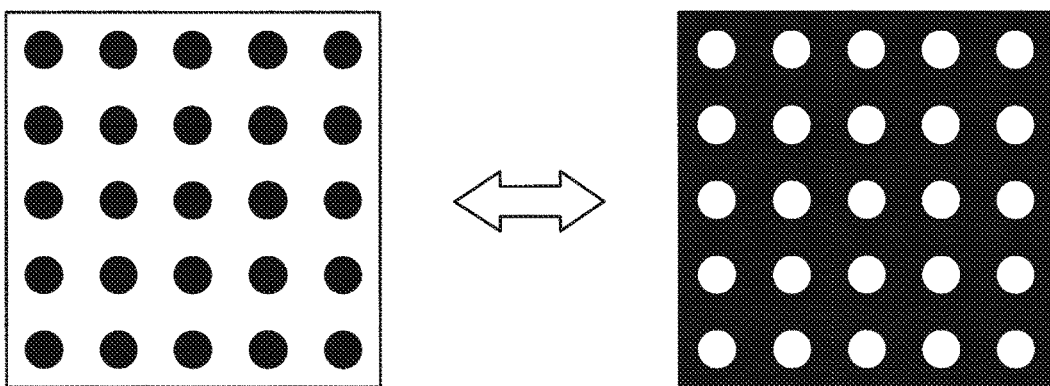
FIG. 2E shows another example intensity distribution of the first illumination light and the temporal change thereof.

The light/dark pattern in FIG. 2E is a dot pattern in which the light portions or the dark portions are circles, and the other is the background.

Figure 2F:
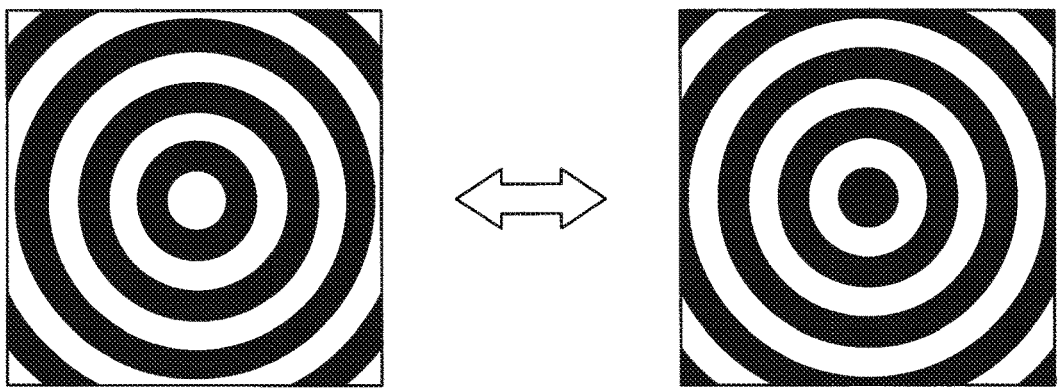
FIG. 2F shows another example intensity distribution of the first illumination light and the temporal change thereof.

The light/dark pattern in FIG. 2F is a concentric circle pattern in which circular band-like light portions and dark portions are alternately repeated in the radial direction.

Figure 3A:
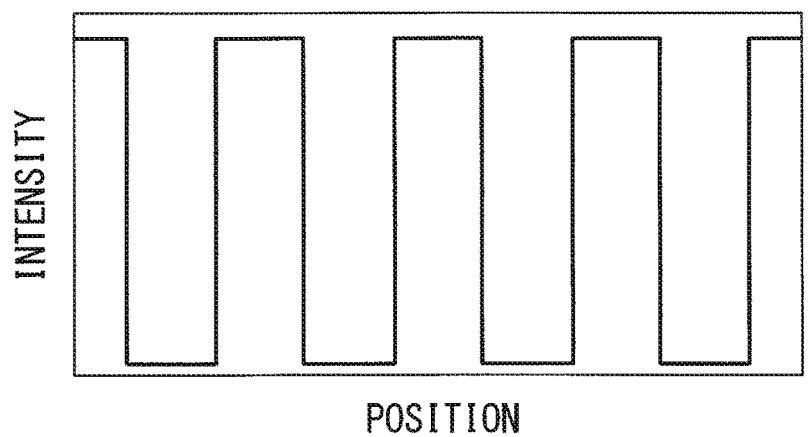
FIG. 3A shows an example spatial profile of the intensity of the first illumination light.
Figure 3B:
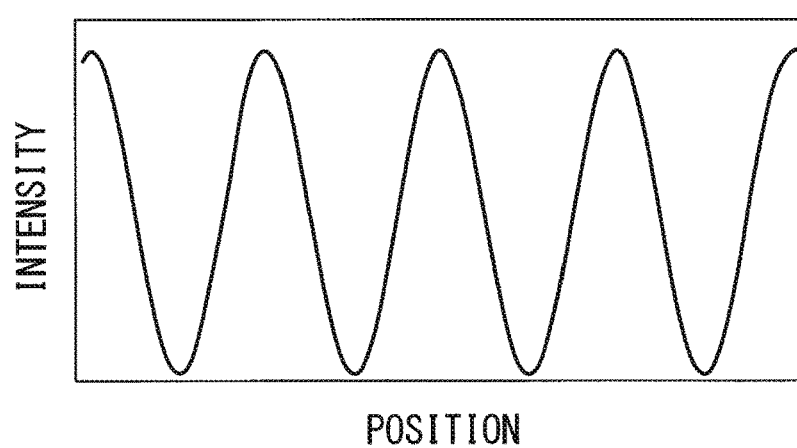
FIG. 3B shows another example spatial profile of the intensity of the first illumination light.
Figure 3C:
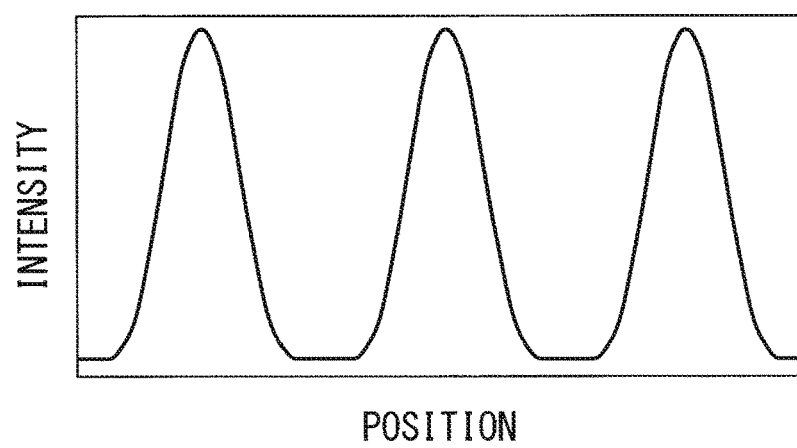
FIG. 3C shows another example spatial profile of the intensity of the first illumination light.
Figure 3D:
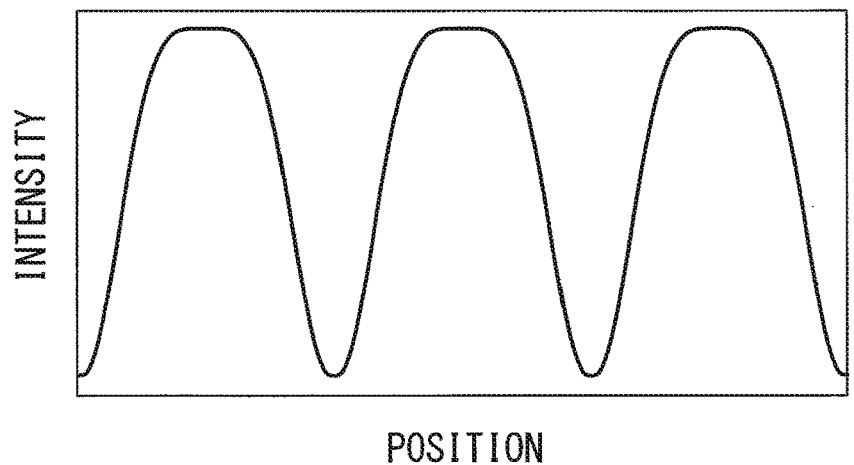
FIG. 3D shows another example spatial profile of the intensity of the first illumination light.
Figure 3E:
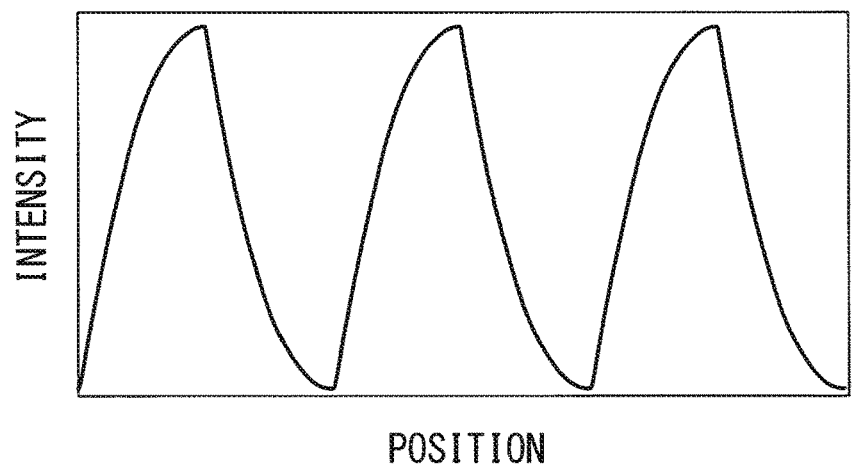
FIG. 3E shows another example spatial profile of the intensity of the first illumination light.
Figure 3F:
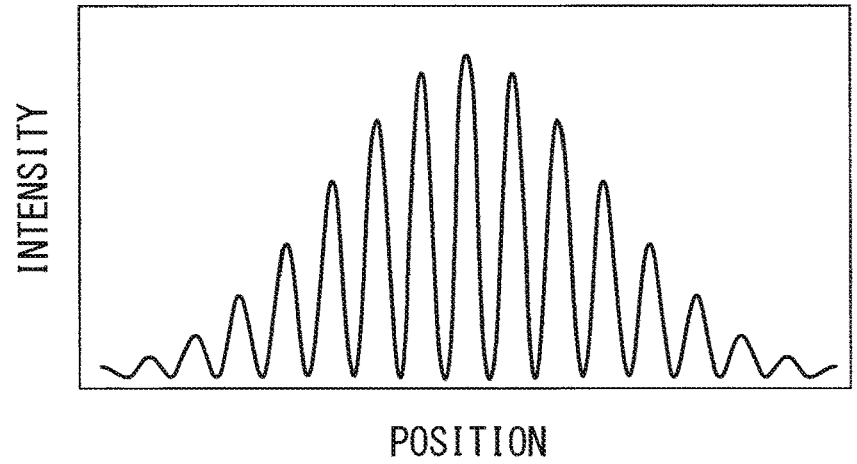
FIG. 3F shows another example spatial profile of the intensity of the first illumination light.

FIGS. 3A to 3F show example intensity profiles showing spatial changes in the intensity I between the light portions and the dark portions in the light/dark patterns in FIGS. 2A to 2F. The horizontal axis shows the position X. The intensity profile may have a rectangular-wave shape, as shown in FIG. 3A, a sine-wave shape, as shown in FIG. 3B, a shape between a rectangular wave and a sine wave, as shown in FIGS. 3C and 3D, or an asymmetric wave shape, as shown in FIG. 3E. As shown in FIG. 3E, the intensity profile may be highest at the center of the first illumination light L1 and may generally decrease from the center toward the periphery. In each of FIGS. 3A to 3E, the period of the light portions and the dark portions may be the distance between a light portion and an adjoining light portion.

The imaging unit 6 includes an imaging lens 6a provided at the distal end of the endoscope 2 to collect light produced by the biological tissue A, and an imaging element 6b for imaging an image of the biological tissue A formed by the imaging lens 6a. The imaging unit 6 performs imaging while the first illumination light L1 is radiated onto the biological tissue A to image a first illumination image and performs imaging while the second illumination light L2 is radiated onto the biological tissue A to image a second illumination image. Therefore, the operations of the illumination units 41 and 42 and the imaging element 6b are controlled by the control unit such that the timing for emitting the illumination light L1 and L2 from the illumination units 41 and 42 and the timing for imaging images with the imaging element 6b are synchronized. The first illumination image and the second illumination image imaged by the imaging element 6b are transmitted from the imaging element 6b to the image processing unit 7.

Figure 4:
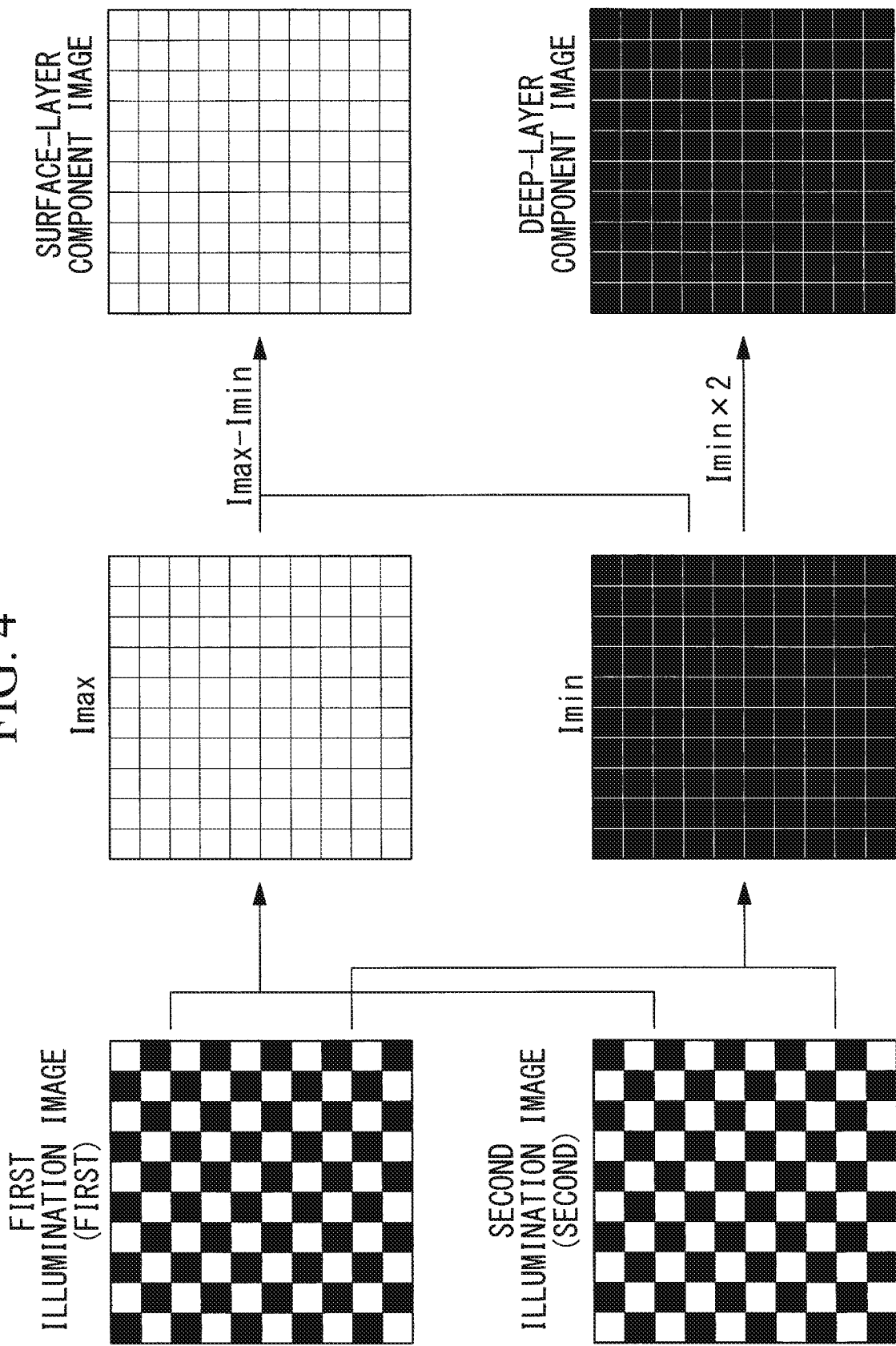
FIG. 4 is a diagram showing processing for generating a surface-layer component image and a deep-layer component image in a separation processing unit.

Herein, the intensity distribution of the first illumination light L1 radiated onto the biological tissue A is changed with time by the intensity-distribution changing unit 5, as shown in FIGS. 2A to 2F. By performing imaging operations at two times at which the light portions and the dark portions of the first illumination light L1 radiated onto the biological tissue A are reversed, the imaging element 6b images two first illumination images in which light-portion projected areas and dark-portion projected areas are reversed so that the light-portion projected areas and the dark-portion projected areas compensate for each other, as shown in FIG. 4. In the first illumination images in FIG. 4, the white areas represent the light-portion projected areas, and the black areas represent the dark-portion projected areas. Accordingly, the operations of the intensity-distribution changing unit 5 and the imaging element 6b are controlled by the control unit such that the timing for changing the intensity distribution with the intensity-distribution changing unit 5 and the timing for imaging images with the imaging element 6b are synchronized.

The image processing unit 7 includes, as functions, a separation processing unit 71 that separates a surface-layer component image (image information) and a deep-layer component image (image information) from the two first illumination images, and a separated-image generating unit 72 that processes the second illumination image using the surface-layer component image and the deep-layer component image to generate a surface-layer image (separated image) and a deep-layer image (separated image).

FIG. 4 shows image processing performed by the separation processing unit 71. For the pixel located at each position in the two first illumination images, an intensity value Imax corresponding to when a light portion is projected and an intensity value Imin corresponding to when a dark portion is projected are imaged. As shown in FIG. 4, the separation processing unit 71 generates a deep-layer component image containing a large amount of information about a deep layer D of the biological tissue A from the intensity values Imin in the two first illumination images and generates a surface-layer component image containing a large amount of information about a surface B and a surface layer C of the biological tissue A from the intensity values Imin and the intensity values Imax in the two first illumination images.

Figure 5:
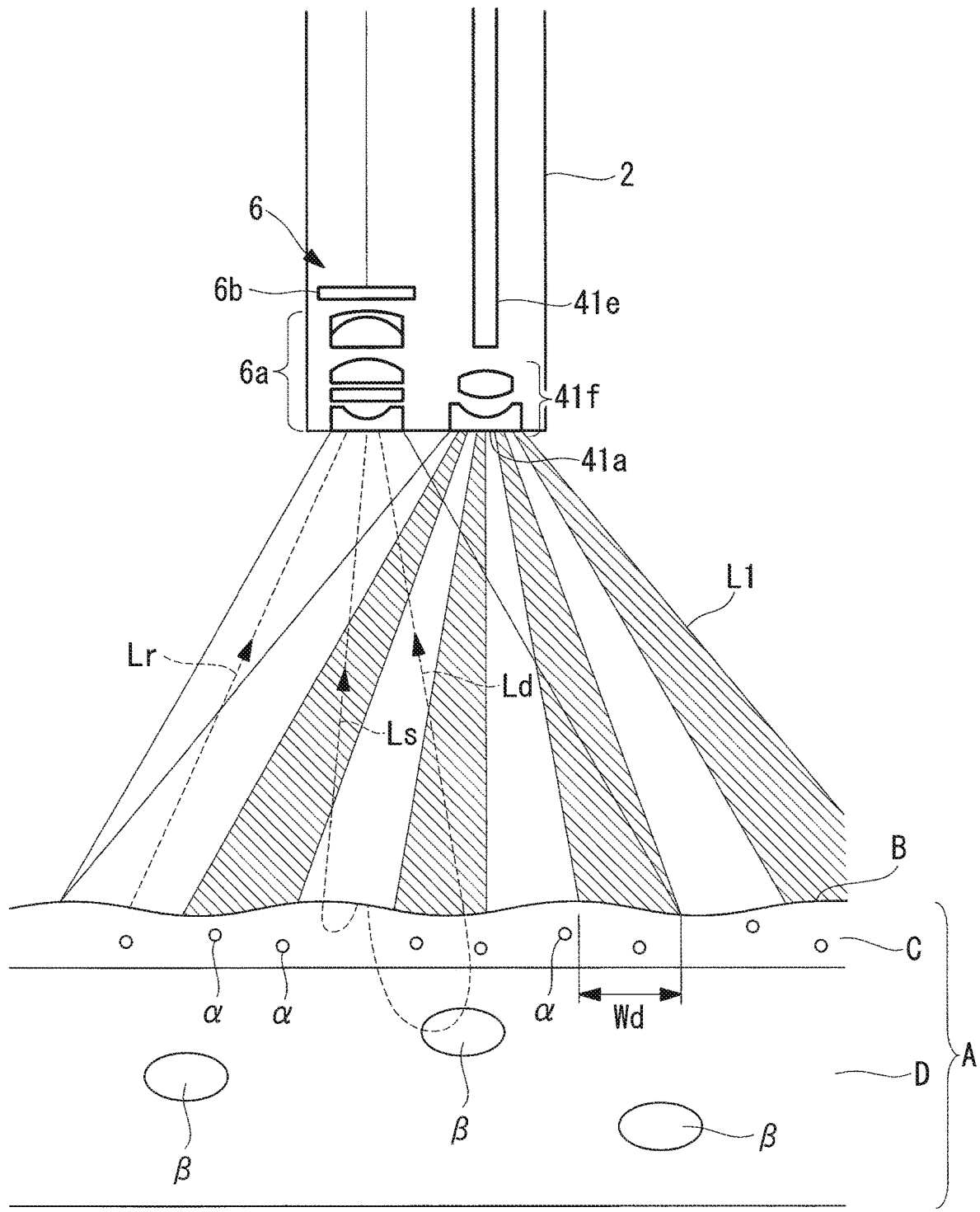
FIG. 5 is a diagram showing the relationship between: specular reflection light, surface scattered light, and internal scattered light produced in biological tissue by being irradiated with the first illumination light; and the positions where these types of light are produced.

The biological tissue A is a scatterer and includes, as shown in FIG. 5, structures α, such as capillaries, in the surface layer C extending from the surface B to a depth of several tens of μm and structures β, such as large blood vessels, in the deep layer D located at a deeper part than the surface layer C. When the first illumination light L1 having a light/dark pattern is radiated on the biological tissue A, the biological tissue A generates specular reflection (specular) light Lr, surface scattered light Ls, and internal scattered light Ld. In FIG. 5, the illustration of the second illumination unit 42 is omitted.

The specular light Lr is reflected light of the first illumination light L1 specularly reflected at the surface B of the biological tissue A and is generated at the light-portion projected areas.

The surface scattered light Ls is scattered light of the first illumination light L1 that has entered the biological tissue A from the light-portion projected areas, has passed through the surface layer C while being repeatedly scattered, and has been emitted from the surface B. Most of the surface scattered light Ls is emitted from the light-portion projected areas.

The internal scattered light Ld is scattered light of the first illumination light L1 that has entered the biological tissue A from the light-portion projected areas, has passed through the deep layer D while being repeatedly scattered, and has been emitted from the surface B. A portion of the internal scattered light Ld is emitted from the light-portion projected areas, and another portion is emitted from the dark-portion projected areas after propagating to the dark-portion projected areas.

As described, the intensity values Imin at the dark-portion projected areas in the two first illumination images are mainly based on the internal scattered light Ld and mainly contain information about the deep layer D. Meanwhile, the intensity values Imax at the light-portion projected areas in the two first illumination images are based on the specular light Lr, the surface scattered light Ls, and the internal scattered light Ld and contain information about the surface B, the surface layer C, and the deep layer D.

Figure 6:
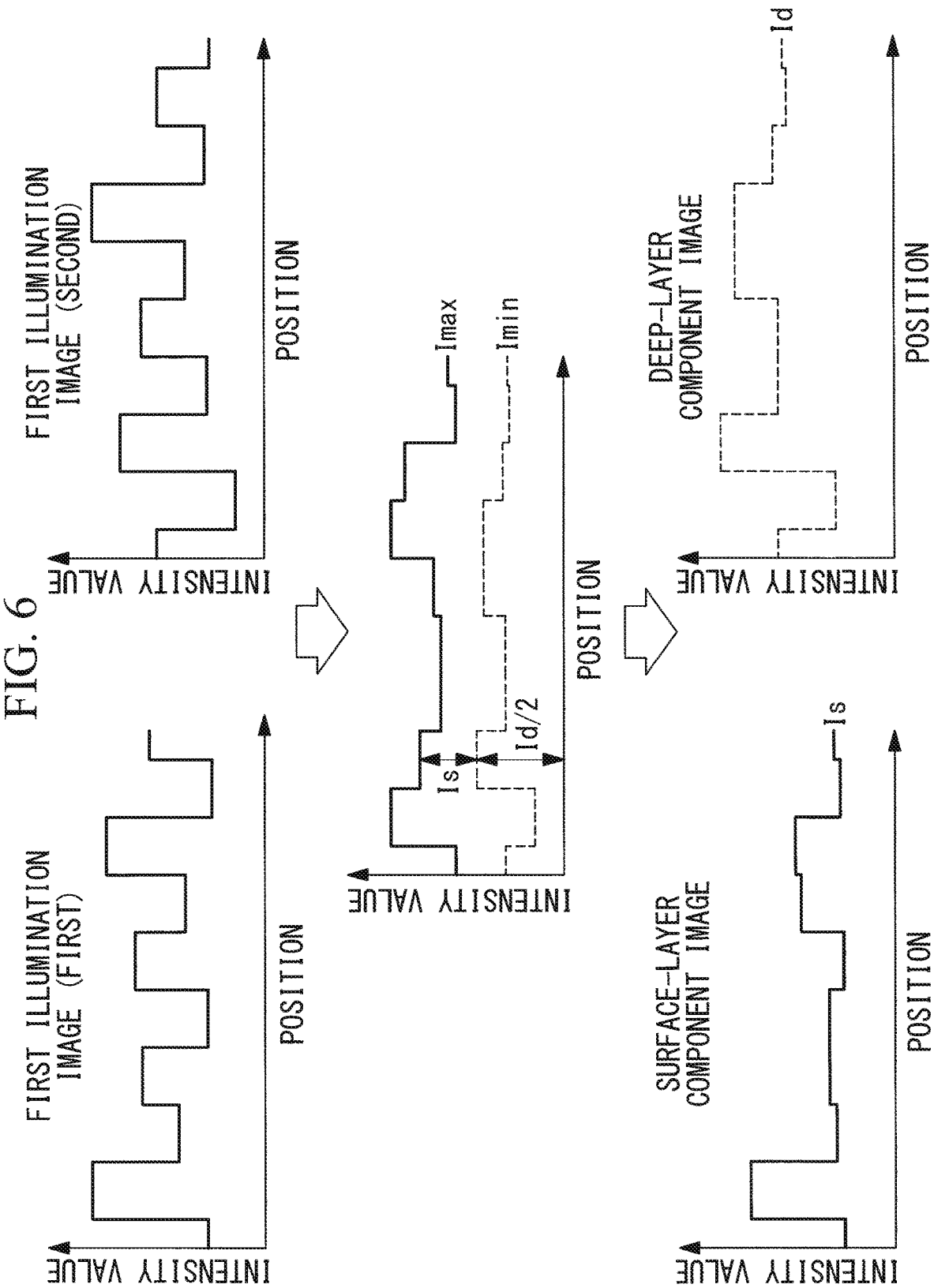
FIG. 6 is a diagram showing a method for generating the surface-layer component image and the deep-layer component image in the separation processing unit.

FIG. 6 shows a detailed method for generating a surface-layer component image and a deep-layer component image by the separation processing unit 71. As shown in FIG. 6, the two first illumination images have brightness distributions in which the intensity value is high at pixels corresponding to the light-portion projected areas, and the intensity value is low at pixels corresponding to the dark-portion projected areas. To simplify the explanation, FIG. 6 shows intensity profiles in the cases where the first illumination light L1 has a light/dark pattern in which, as in the light/dark pattern in FIG. 2A or 2B, the light portions and the dark portions are repeated at regular periods, and the boundaries between the pixels in the image and the boundaries between the light portions and the dark portions in the light/dark pattern coincide (that is, one light portion or dark portion corresponds to one pixel).

As described above, for each pixel, two intensity values, Imax and Imin, can be obtained from the two first illumination images. For each pixel, the separation processing unit 71 defines the higher intensity value as the intensity value Imax and the lower intensity value as the intensity value Imin. Next, the separation processing unit 71 calculates an intensity value Is of each pixel of the surface-layer component image and an intensity value Id of the pixel of the deep-layer component image from the expression below to generate a surface-layer component image having the intensity value Is and a deep-layer component image having the intensity value Id.

$$Is = Imax - Imin$$

$$Id = Imin \times 2$$

As a result, a deep-layer component image having the intensity value Imin, which mainly contains information about the deep layer D, is generated. By subtracting the intensity value Imin from the intensity value Imax, the information about the deep layer D is removed, and a surface-layer component image having the intensity value Is, which mainly contains information about the surface B and the surface layer C, is generated.

Figure 7:
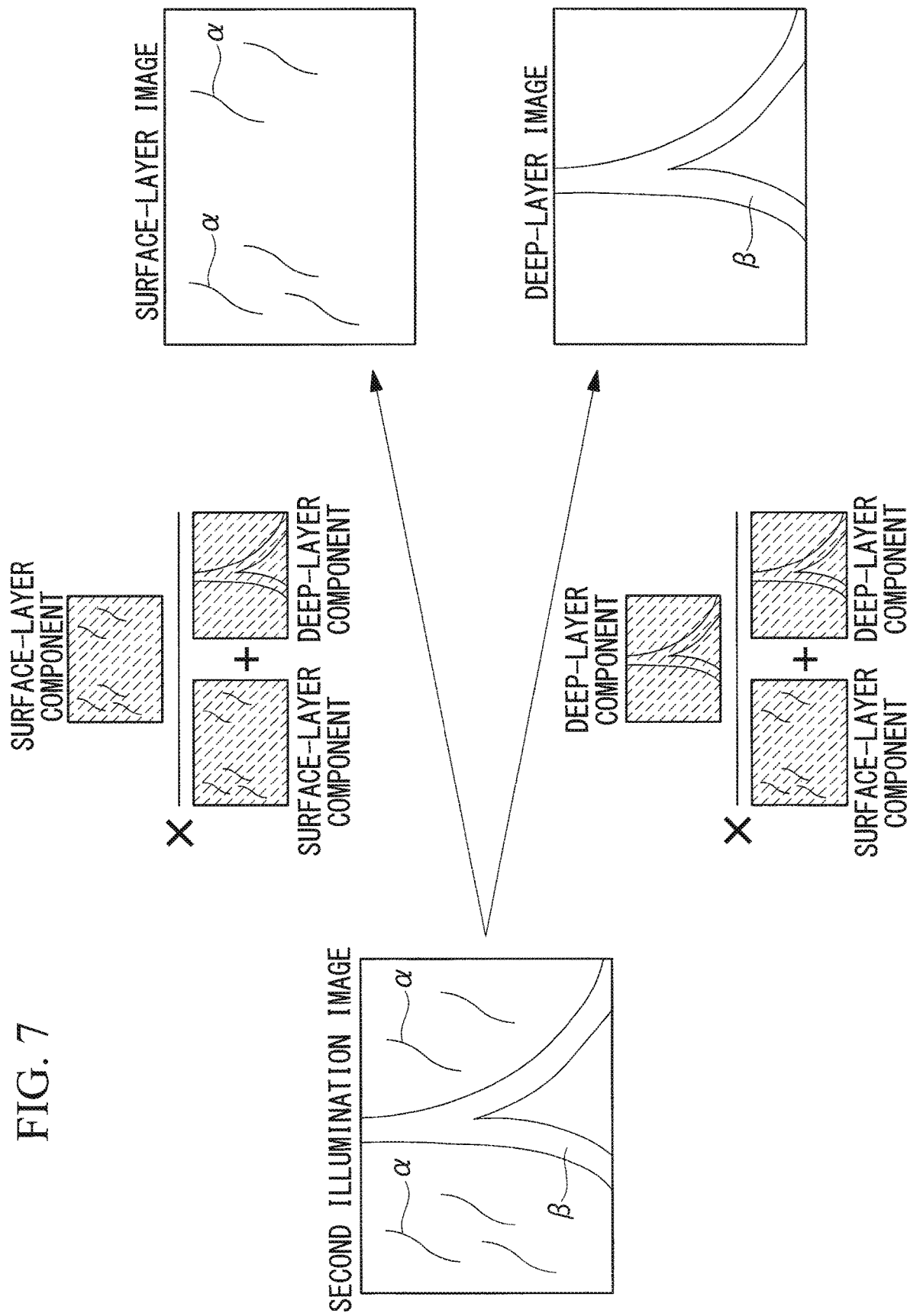
FIG. 7 is a diagram showing processing for generating the surface-layer image and the deep-layer image in a separated-image generating unit.

As shown in FIG. 7, the separated-image generating unit 72 generates a surface-layer image on the basis of Expression (a) below and generates a deep-layer image on the basis of Expression (b) below.

Surface-layer image=second illumination image×
surface-layer component image/(surface-layer
component image+deep-layer component
image)  (a)

Deep-layer image=second illumination image×deep-
layer component image/(surface-layer compo-
nent image+deep-layer component image)  (b)

Specifically, the separated-image generating unit 72 generates a surface-layer image by calculating the proportion of the surface-layer component image in the sum of the surface-layer component image and the deep-layer component image and multiplying the calculated proportion by the second illumination image. The separated-image generating unit 72 generates a deep-layer image by calculating the proportion of the deep-layer component image in the sum of the surface-layer component image and the deep-layer component image and multiplying the calculated proportion by the second illumination image.

The surface-layer image and the deep-layer image generated by the separated-image generating unit 72 are output from the body part 3 to a display device (not shown) connected to the body part 3 and are displayed on the display device.

This image processing unit 7 is realized as, for example, an image processing program executed by a computer. Specifically, the body part 3 accommodates a central processing unit (CPU), a main memory, such as a RAM, and an auxiliary storage, such as a hard-disk drive. An image processing program for causing the CPU to execute the above-described processing by the image processing unit 7 is stored in the auxiliary storage. As a result of the image processing program being loaded from the auxiliary storage into the main memory, and the CPU executing the processing in accordance with the image processing program, the above-described function of the image processing unit 7 is realized.

When the second illumination light L2, which is ordinary white light having a spatially substantially uniform intensity distribution, is radiated onto the biological tissue A, the specular light Lr, the surface scattered light Ls, and the internal scattered light Ld enter the imaging unit 6 in a superimposed state. Hence, the second illumination image, which is obtained by imaging an image of the biological tissue A illuminated with the second illumination light L2, shows both the structures α, such as capillaries, in the surface layer C extending from the surface B to a depth of several tens of μm and the structures β, such as large blood vessels, in the deep layer D.

In contrast, when the first illumination light L1 having a light/dark pattern is radiated onto the biological tissue A, the internal scattered light Ld containing a large amount of information about the deep layer D is spatially separated from the specular light Lr and the surface scattered light Ls containing information about the surface B and the surface layer C, and a first illumination image, in which the area where the information about the deep layer D is dominant is spatially separated from the area containing a large amount of information about the surface B and the surface layer C, is obtained. From this first illumination image, a surface-layer component image, which mainly contains information about the surface B and the surface layer C and in which images of the structures α are emphasized, and a deep-layer component image, which mainly contains information about the deep layer D and in which images of the structures β are emphasized, can be separated.

Although it may be difficult to ensure a sufficient level of structured first illumination light L1 due to the design limitation or the like of the first illumination unit 41, it is easy to ensure a sufficient level of second illumination light L2, which is ordinary white light, and thus, it is possible to image a bright second illumination image. According to this embodiment, by correcting this bright second illumination image with the surface-layer component image and the deep-layer component image to generate the surface-layer image and the deep-layer image, a bright surface-layer image and a deep-layer image can be generated, which is advantageous.

The amount of information about the surface layer C in the surface-layer image and the amount of information about the deep layer D in the deep-layer image depend on the width Wd (see FIG. 5) of the dark portions on the surface B of the biological tissue A. More specifically, the larger the width Wd of the dark portions is, the larger the amount of information about the surface layer C that can be imaged as the surface-layer image is, because the depth of the surface layer C is greater than that when the width Wd of the dark portions is small, whereas the larger the width Wd of the dark portions is, the less the amount of information about the deep layer D is, because the depth of the deep layer D is constant regardless of the width Wd of the dark portions. To ensure good balance between the amount of information about the surface layer C in the surface-layer image and the amount of information about the deep layer D in the deep-layer image, it is desirable that the width Wd of the dark portions on the surface B of the biological tissue A be from 0.005 mm to 25 mm.

When the width Wd of the dark portions is less than 0.005 mm, the proportion of the internal scattered light Ld that spreads from the light-portion projected areas into the dark-portion projected areas increases. As a result, the difference between the intensity value Imax and the intensity value Imin decreases, potentially leading to a lack of information about the surface layer C contained in the surface-layer component image and the surface-layer image. On the other hand, when the width Wd of the dark portions is greater than 25 mm, the internal scattered light Ld cannot reach the central portions of the dark-portion projected areas. As a result, the intensity value Imin approaches zero, potentially leading to a lack of information about the deep layer D contained in the deep-layer component image and the deep-layer image.

In this embodiment, in generating the surface-layer image, the separated-image generating unit 72 may multiply the surface-layer component image by a coefficient P, as shown in Expression (a') below. In generating the deep-layer image, the separated-image generating unit 72 may multiply the deep-layer component image by a coefficient Q, as shown in Expression (b') below.

Surface-layer image=second illumination image×P× surface-layer component image/(surface-layer component image+deep-layer component image)   (a')

Deep-layer image=second illumination image×Q× deep-layer component image/(surface-layer component image+deep-layer component image)   (b')

This makes it possible to generate a surface-layer image in which information about the surface layer is further emphasized in accordance with the coefficient P and to generate a deep-layer image in which information about the deep layer is further emphasized in accordance with the coefficient Q.

The separated-image generating unit 72 may also combine the surface-layer image and the deep-layer image to generate a combined image. In this case, by setting one of the coefficients P and Q to a large value, it is possible to generate a combined image in which one of the information about the surface layer C and the information about the deep layer D is emphasized, while preserving both sets of information. More specifically, by increasing the coefficient P, it is possible to obtain a combined image in which the information about the surface layer C is emphasized, and by increasing the coefficient Q, it is possible to obtain a combined image in which the information about the deep layer D is emphasized. Similarly, by setting one of the coefficients P and Q to a small value, it is possible to generate a combined image in which one of the information about the surface layer C and the information about the deep layer D is deemphasized while preserving both sets of information.

For example, the coefficients P and Q are set by a user through input means (not shown) connected to the body part 3.

The coefficients P and Q may be set for each pixel. The intensity value Iij of each pixel ij in the combined image can be calculated from the expression below. Herein, ij (i=1, 2, . . . , n, j=1, 2, . . . , m) are the position coordinates of a pixel in an image of n pixels×m pixels. In the expression below, Pij is the combining ratio of the pixels ij in the surface-layer image, and Qij is the combining ratio of the pixels ij in the deep-layer image.

$$Iij=Pij*Isij/(Isij+Idij)+Qij*Idij/(Isij+Idij)$$

For example, the system may be configured such that a user can set the combining ratios Pij and Qij while observing the surface-layer image and the deep-layer image displayed on the display device.

The coefficients P and Q may be set for each wavelength. The intensity value Ik of a wavelength λk (k=1, 2, . . . , 1) of a combined image can be calculated from the expression below. Isk is the intensity value of the wavelength λk of the surface-layer image, Idk is the intensity value of the wavelength λk of the deep-layer image, Pk is the combining ratio of the wavelength λk of the surface-layer image, and Qk is the combining ratio of the wavelength λk of the deep-layer image.

$$Ik=Pk*Isk/(Isk+Idk)+Qk*Idk/(Isk+Idk)$$

For example, the system may be configured such that a user can set the combining ratios Pk and Qk while observing the surface-layer image and the deep-layer image displayed on the display device.

In this embodiment, although the intensity-distribution changing unit 5 may alternately change, in a discontinuous manner, the intensity distribution of the first illumination light L1 between two light/dark patterns in which the light portions and the dark portions are reversed, as shown in FIGS. 2A to 2F, instead, the intensity-distribution changing unit 5 may change the intensity distribution of the first illumination light L1 between the two light/dark patterns in a continuous manner.

When the light/dark pattern is change in a continuous manner like this, the imaging unit 6 may perform imaging at three or more different times at which the positions of the light portions and the dark portions are different from each to image three or more first illumination images in which the positions of the light-portion projected areas and the dark-portion projected areas are different from each other. The separation processing unit 71 may generate the surface-layer component image and the deep-layer component image from the three or more first illumination images. In this case, because three or more intensity values are obtained for the pixel at each position, the maximum intensity value may be calculated as Imax, and the minimum intensity value may be calculated as Imin.

Figure 8:
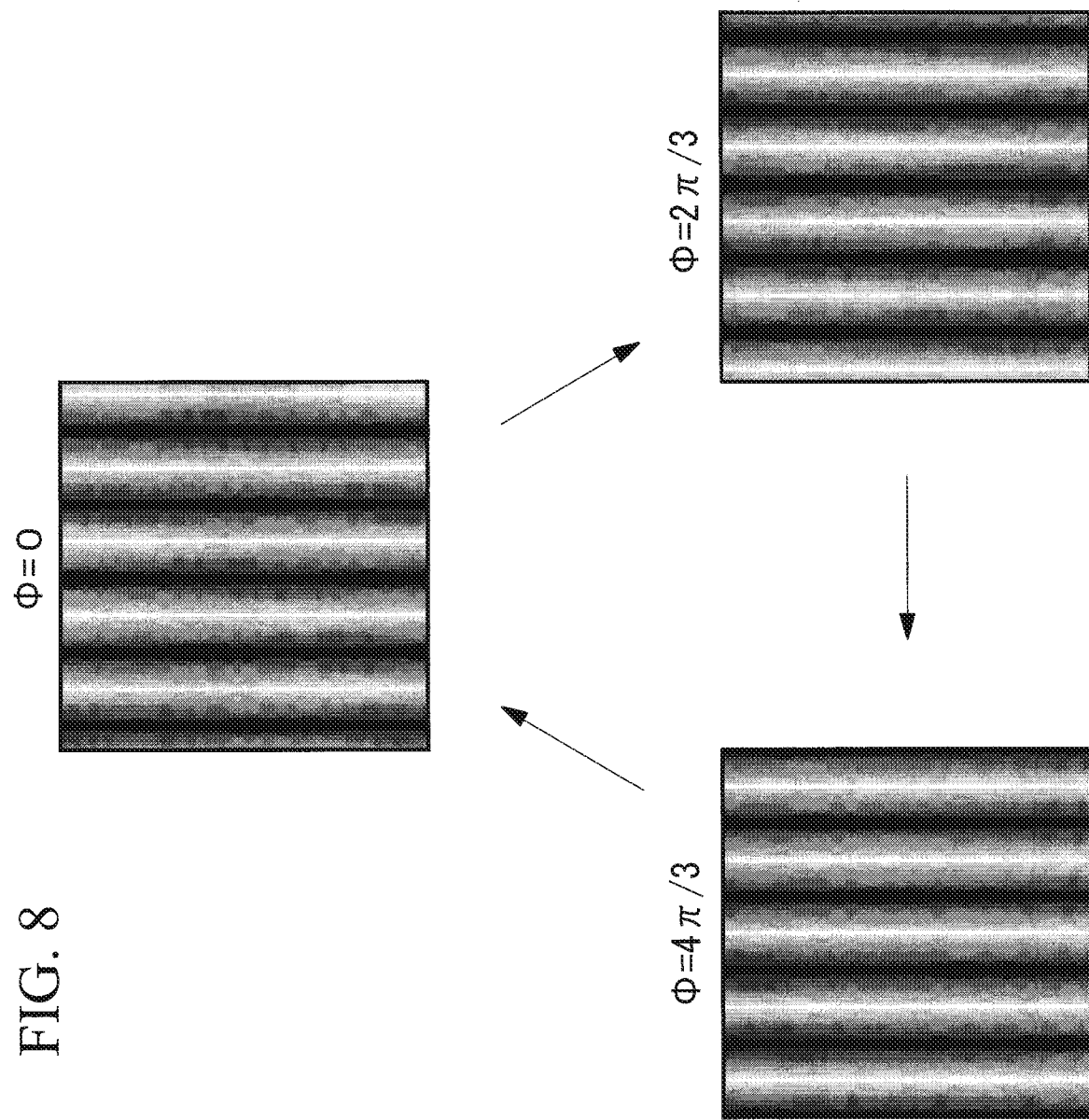
FIG. 8 is a diagram showing a method for calculating intensity values Imax and Imin by using a phase shift method.

In this embodiment, although the intensity values in the two first illumination images are used as the intensity values Imax and Imin, when the light/dark pattern is a linear stripe pattern in which the intensity changes in the form of a sine wave, as shown in FIGS. 2B and 3B, the intensity values Imax and Imin of each pixel may be calculated by using a phase shift method. By using the phase shift method, the maximum intensity value Imax and the minimum intensity value Imin of each pixel can be calculated from three first illumination images having different light/dark pattern phases Φ, as shown in FIG. 8. Accordingly, it is possible to generate a surface-layer image and a deep-layer image having the same resolution as the second illumination image by using a small number of first illumination images.

In this embodiment, although the first illumination light L1 having a light/dark pattern structured by the liquid-crystal element provided in the body part 3 is generated, the configuration of the first illumination unit 41 is not limited thereto, and the first illumination light L1 may be generated by another method.

Figure 9A:
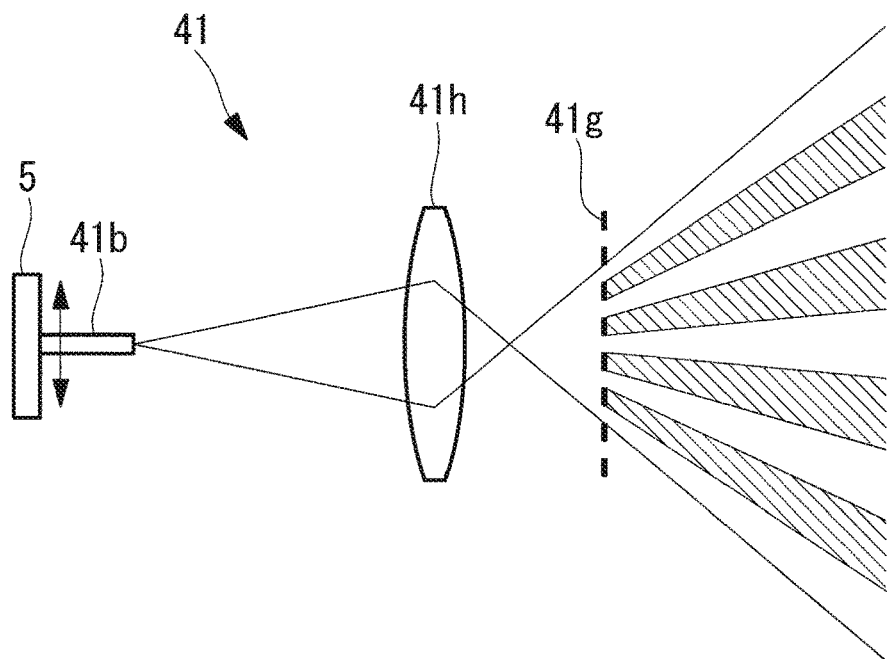
FIG. 9A shows another configuration example of a first illumination unit and an intensity-distribution changing unit.
Figure 9B:
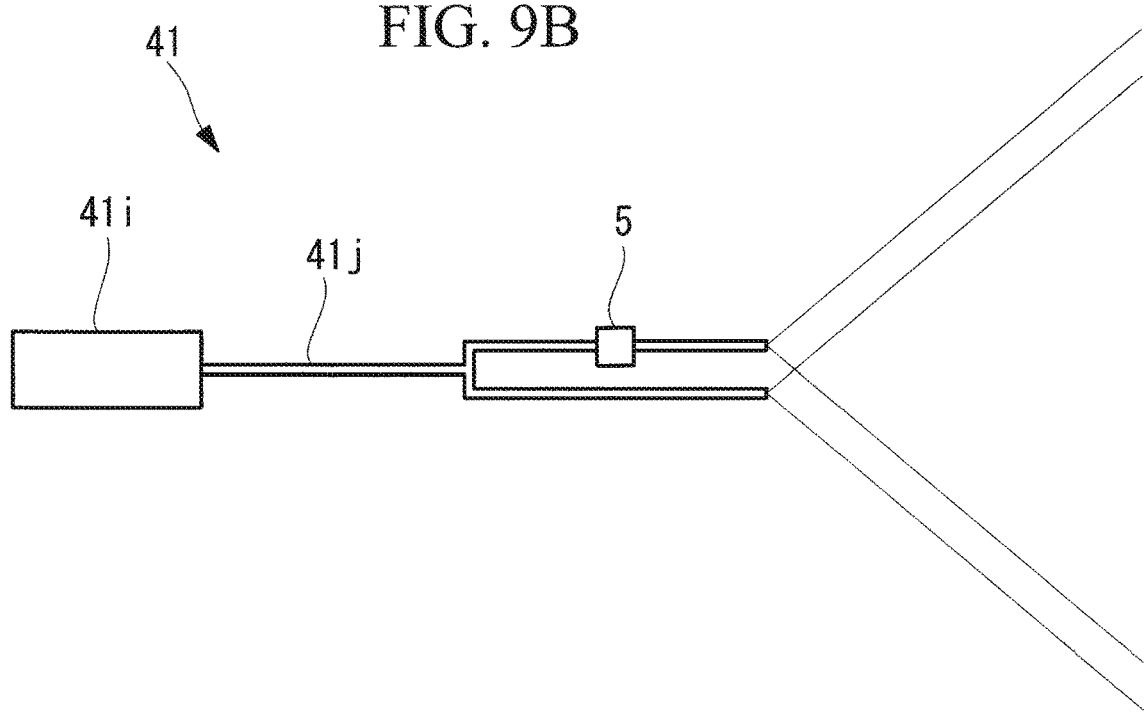
FIG. 9B shows another configuration example of the first illumination unit and the intensity-distribution changing unit.
Figure 9C:
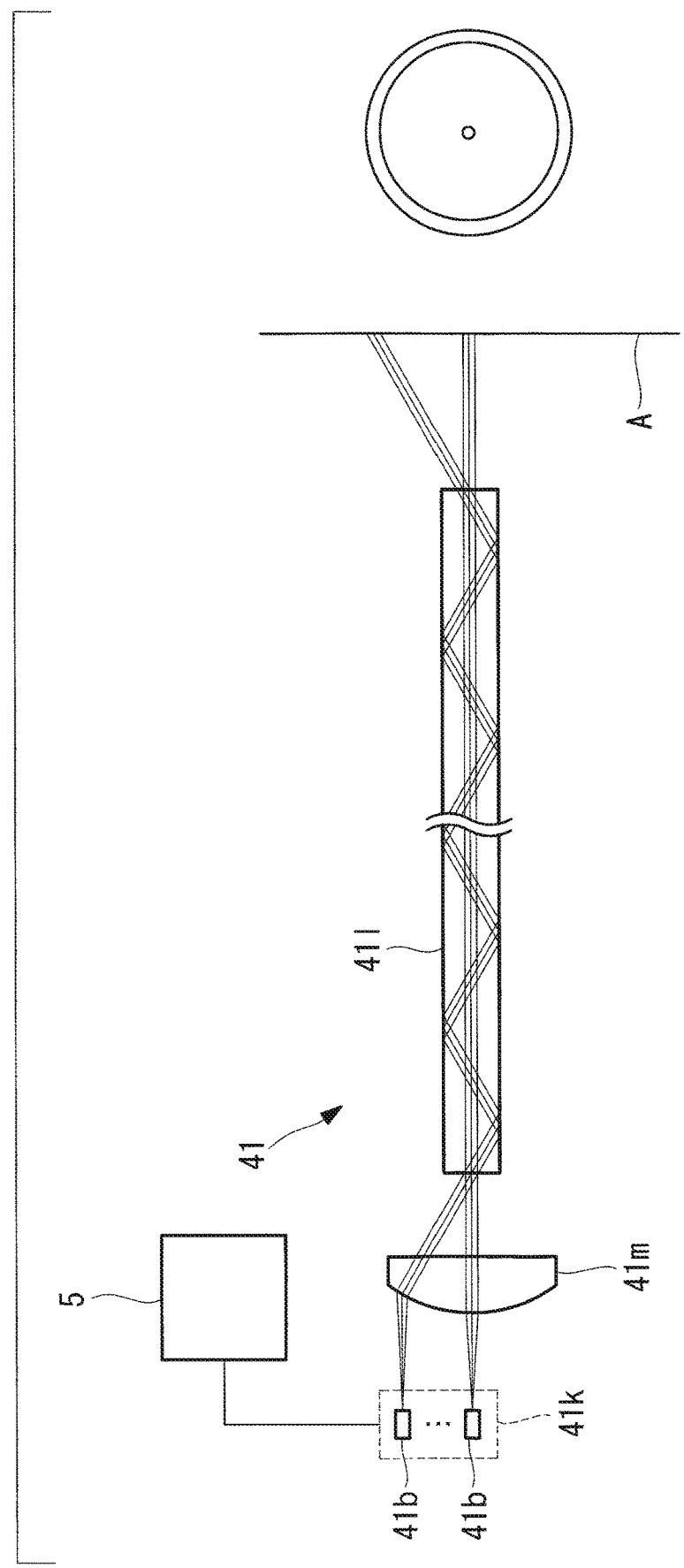
FIG. 9C shows another configuration example of the first illumination unit and the intensity-distribution changing unit.

FIGS. 9A to 9C show modifications of the configuration of the first illumination unit 41 and the intensity-distribution changing unit 5.

The first illumination unit 41 in FIG. 9A forms a light/dark pattern on the surface B of the biological tissue A as in a shadowgraph and includes a light source 41b and a mask 41g provided at the distal end portion of the endoscope 2.

The mask 41g is, for example, a light-shielding substrate provided with openings, serving as light-transmission areas, or a transparent substrate provided with a light-shielding film, serving as light-blocking areas. When the white light output from the light source 41b passes through the mask 41g, the first illumination light L1 having a light/dark pattern is generated, and the projection pattern of the mask 41g is projected on the biological tissue A. A lens 41h that changes the divergence angle of the white light such that the illumination light L1 radiated on the biological tissue A has a desired divergence angle may be provided between the light source 41b and the mask 41g.

By making the intensity-distribution changing unit 5 serve as an actuator for moving at least one of the light source 41b and the mask 41g to relatively move the light source 41b and the mask 41g in a direction intersecting the optical axis of the white light, the intensity distribution can be changed with time.

The intensity-distribution changing unit 5 may alternatively be made to serve as a control device for controlling turning on and off of a plurality of light sources 41b so as to turn on some of the light sources 41b, instead of moving a single light source 41b. Specifically, by arraying the plurality of light sources 41b in a direction substantially parallel to the mask 41g and making the intensity-distribution changing unit 5 switch the light sources 41b to be turned on, it is possible to change the intensity distribution with time.

The first illumination unit 41 in FIG. 9B uses an interference fringe of light as the light/dark pattern and includes a laser light source 41i and an optical path 41j that splits the light output from the laser light source 41i into two and emits two rays of light. The optical path 41j is formed of, for example, an optical fiber. When the two rays of light emitted from the optical path 41j interfere with each other, interference fringes having a sine-wave-shaped intensity profile, serving as a light/dark pattern, are formed. The intensity-distribution changing unit 5, which is provided in one of the optical paths of the two rays of light split, is an optical device that changes the optical path length. The intensity-distribution changing unit 5 shifts the position of the interference fringes in a direction perpendicular to the optical axis of the illumination light by changing the length of one of the optical paths of the two rays of light.

The first illumination unit 41 in FIG. 9C includes a light source array 41k and a light guide member 41l that guides the light while preserving the angle of incidence of the light with respect to the optical axis thereof. The light source array 41k has a plurality of light sources 41b arranged such that the angles of incidence of light with respect to the entrance end of the light guide member 41l are different from each other. Although the plurality of light sources 41b are arranged in a line in FIG. 9C, the plurality of light sources 41b may be arranged two-dimensionally. An example light guide member 41l is a rod lens or a multi-mode fiber.

The rays of white light emitted from the light sources 41b are converted into parallel beams by the lens 41m and enter the entrance end of the light guide member 41l. The beams that have entered the light guide member 41l are guided through the light guide member 41l while preserving their angles and are emitted from the exit end of the light guide member 41l toward the biological tissue A at the same angles as the angles at which the beams entered the entrance end. Because the beams diffuse in the circumferential direction while being repeatedly reflected in the light guide member 41l, the beams emitted from the light guide member 41l form a circular shape. Accordingly, by simultaneously turning on the plurality of light sources 41b, first illumination light L1 having a concentric circle pattern, as shown in FIG. 2F, is generated.

The intensity-distribution changing unit 5 is a control device for controlling turning on and off of the light sources 41b. The intensity-distribution changing unit 5 changes the intensity distribution by controlling turning on and off of the respective light sources 41b to switch the light sources 41b to be turned on.

Instead of switching the light sources 41b to be turned on, the intensity-distribution changing unit 5 may be made to serve as an actuator for moving the light sources 41b in a direction intersecting the optical axis.

In this embodiment, it is desirable that the first illumination unit 41 emit divergent first illumination light L1 toward the biological tissue A such that the light/dark pattern projected on the surface B of the biological tissue A is magnified in proportion to the imaging distance between the biological tissue A and the imaging unit 6.

The boundary between the depth of the information contained in the surface-layer component image and the depth of the information contained in the deep-layer component image depends on the period of the light portions and the dark portions. The larger the period of the light portions and the dark portions is, the deeper the position of the boundary is, and thus, the larger the amount of information contained in the surface-layer component image is. Accordingly, by changing the imaging distance to magnify or reduce the light/dark pattern on the surface B of the biological tissue A, the surface-layer component image and the deep-layer component image containing the information at different depths can be imaged.

Although the period of the light portions and the dark portions on the surface B of the biological tissue A may be changed by changing the imaging distance to magnify or reduce the overall light/dark pattern, the spatial period of the light portions and the dark portions in the light/dark pattern of the first illumination light L1 may be changed.

For example, the period of the light portions and the dark portions may be changed by electrically controlling the liquid-crystal element 41c provided in the first illumination unit 41.

Three or more separated images may be generated by using two or more first illumination images imaged by radiating the first illumination light L1 in which the spatial period of the light portions and the dark portions, that is, the width of the dark portions, varies. Specifically, the separation processing unit 71 may separate three or more component images containing information at different depths from two or more first illumination images, and the separated-image generating unit 72 may generate three or more separated images containing information at different depths by using the three or more component images.

When the light/dark pattern is formed by means of projection, as shown in FIG. 9A, the period of the light portions and the dark portions may be changed by relatively moving the light sources 41b and the mask 41g in the optical axis direction of the white light to change the distance between the light sources 41b and the mask 41g.

Alternatively, a zoom lens including a plurality of lenses, at least one of which is movable in the optical axis direction, may be provided on the optical path of the first illumination light L1.

Although the first illumination unit 41 emits the white first illumination light L1 in this embodiment, the first illumination light L1 is not limited to the white light and may be light having other wavelength characteristics. Examples of the first illumination light L1 include infrared light, monochromatic light, such as red, green, or blue light, and light having a single wavelength. Alternatively, the first illumination light L1 may be composed of a plurality of light having different wavelengths and may be, for example, white light formed by mixing three light, namely, red, green and blue light.

The shape of the wavelength spectrum of the first illumination light L1 may be different from the shape of the wavelength spectrum of the second illumination light L2.

In general, light having a shorter wavelength is more strongly scattered by a scatterer. Accordingly, short wavelength light is less likely to reach the deep layer D of the biological tissue A than long wavelength light, and the information contained in the internal scattered light Ld of the short wavelength light is information at a position shallower than the internal scattered light Ld of the long wavelength light.

Figure 10:
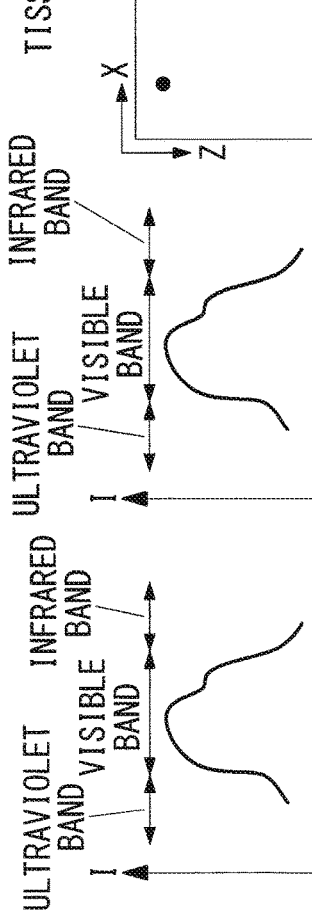
FIG. 10 is a diagram showing the relationships between the shapes of the wavelength spectra of the first and second illumination light; and the contrasts of the surface-layer component image and the deep-layer component image.
Figure 10:
Figure 10:
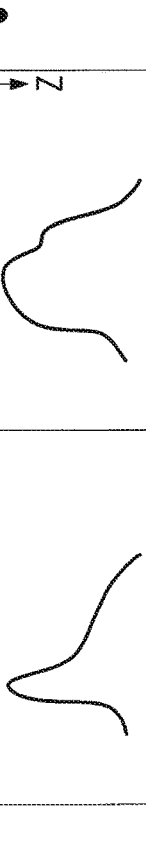
Figure 10:
Figure 10:
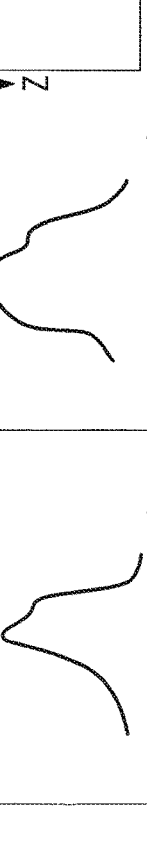

FIG. 10 schematically shows the relationships between the shapes of the wavelength spectra of the illumination light L1 and L2 and the contrasts of the surface-layer component image and the deep-layer component images.

As shown in the top row in FIG. 10, when the shape of the wavelength spectrum of the first illumination light L1 is the same as the shape of the wavelength spectrum of the second illumination light L2, the contrasts of the surface-layer component image and the deep-layer component image are substantially equal to each other. Hence, by using the surface-layer component image and the deep-layer component image in this state, a natural surface-layer image and deep-layer image can be generated.

On the other hand, as shown in the middle row in FIG. 10, by using the first illumination light L1 having an intensity distribution shifted toward the short wavelength side compared with the second illumination light L2, it is possible to generate a surface-layer image in which the contrast of the surface-layer component image is increased to further emphasize the information about the surface layer. Furthermore, as shown in the bottom row in FIG. 10, by using the first illumination light L1 having an intensity distribution shifted toward the long wavelength side compared with the second illumination light L2, it is possible to generate a deep-layer image in which the contrast of the deep-layer component image is increased to further emphasize the information about the deep layer.

Although the information about the surface layer in the surface-layer image and the information about the deep layer in the deep-layer image can also be emphasized by increasing the coefficients P and Q as described above, by controlling the wavelength of the first illumination light L1, it is possible to generate a surface-layer image and a deep-layer image that does not evoke a feeling of strangeness, unlike the electrical emphasis as described above.

When light, such as infrared light, having a different wavelength band from the wavelength band of the second illumination light L2 is used as the first illumination light L1, the first illumination unit 41 and the second illumination unit 42 may simultaneously radiate the first illumination light L1 and the second illumination light L2 onto the biological tissue A, and the imaging unit 6 may image images of the biological tissue A irradiated with both the first illumination light L1 and the second illumination light L2 to simultaneously image the first illumination image and the second illumination image. The imaging unit 6 is configured to separate the light produced by the biological tissue A by being irradiated with the first illumination light L1 and the light produced by the biological tissue A by being irradiated with the second illumination light L2 in accordance with the wavelength and to separately image images thereof.

By imaging the first illumination image and the second illumination image in a single imaging operation like this, it is possible to increase the frame rate of the surface-layer image and the deep-layer image.

Figure 11:
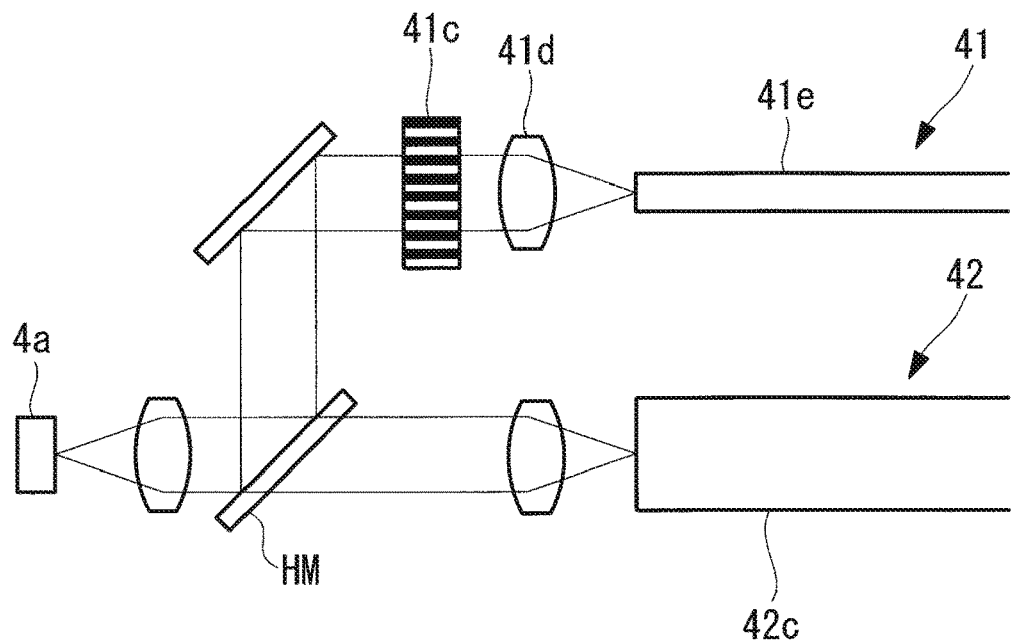
FIG. 11 shows another configuration example of the first illumination unit and the second illumination unit.

In this embodiment, although the first illumination unit 41 and the second illumination unit 42 have the light source 41b and the light source 42b, respectively, instead, as shown in FIG. 11, the first illumination unit 41 and the second illumination unit 42 may have a single common light source 4a. The white light output from the light source 4a is divided into two by a half mirror HM and is distributed between the first illumination unit 41 and the second illumination unit 42.

By making the first illumination unit 41 and the second illumination unit 42 use a common light source as in this configuration, first illumination light L1 and second illumination light L2 having the same wavelength spectrum can be generated. By reducing the number of the light sources 4a, the cost and size of the device can be reduced.

Figure 12:
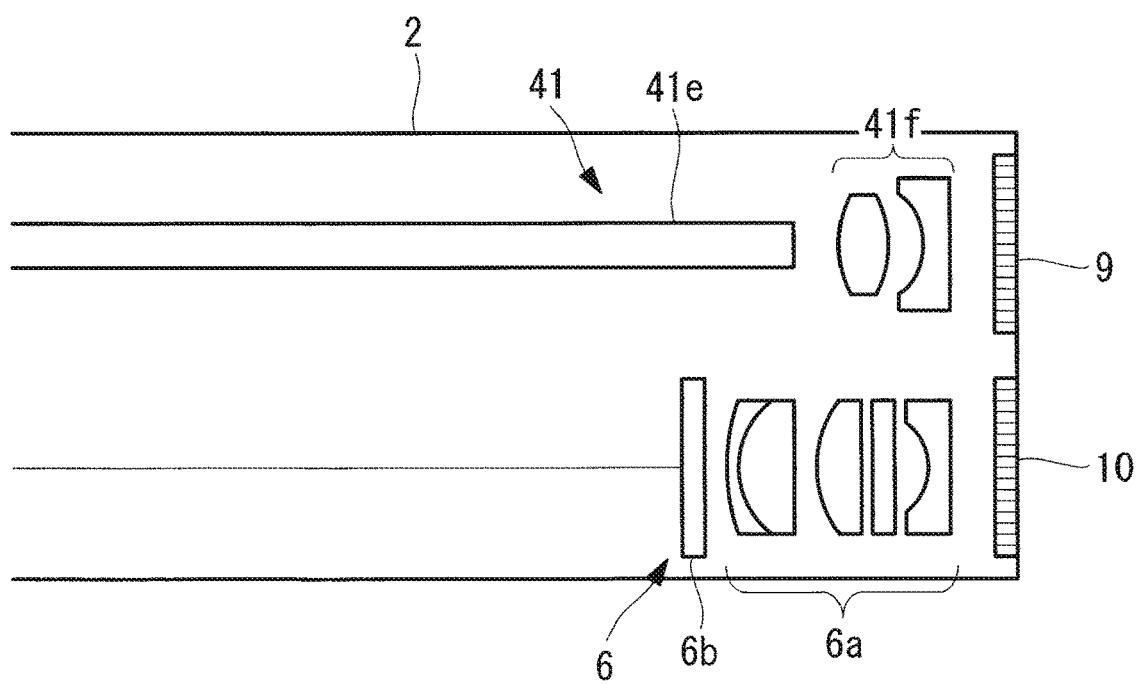
FIG. 12 is a shows the configuration of a part of a modification of an endoscope system having a polarizer.

In this embodiment, although the information about the biological tissue A is separated into two, namely, the information about the surface B and the surface layer C and the information about the deep layer D, it is possible to further separate the information about the surface B and the information about the surface layer C by using polarization, as shown in FIG. 12. In FIG. 12, the illustration of the second illumination unit 42 is omitted.

The endoscope 2 includes, at the distal end thereof, a polarizer 9 that controls the polarizing state of the first illumination light L1 emitted from the first illumination unit 41, and a polarizer 10 that selects the polarizing state of the light produced by the biological tissue A and entering the imaging unit 6. By aligning the polarizing direction of the polarizer 10 with the polarizing direction of the polarizer 9, a first illumination image containing the surface scattered light Ls and the specular light Lr can be imaged, and, by arranging the polarizing direction of the polarizer 10 perpendicular to the polarizing direction of the polarizer 9, a first illumination image not containing the specular light Lr, but containing the surface scattered light Ls can be imaged.

Figure 13:
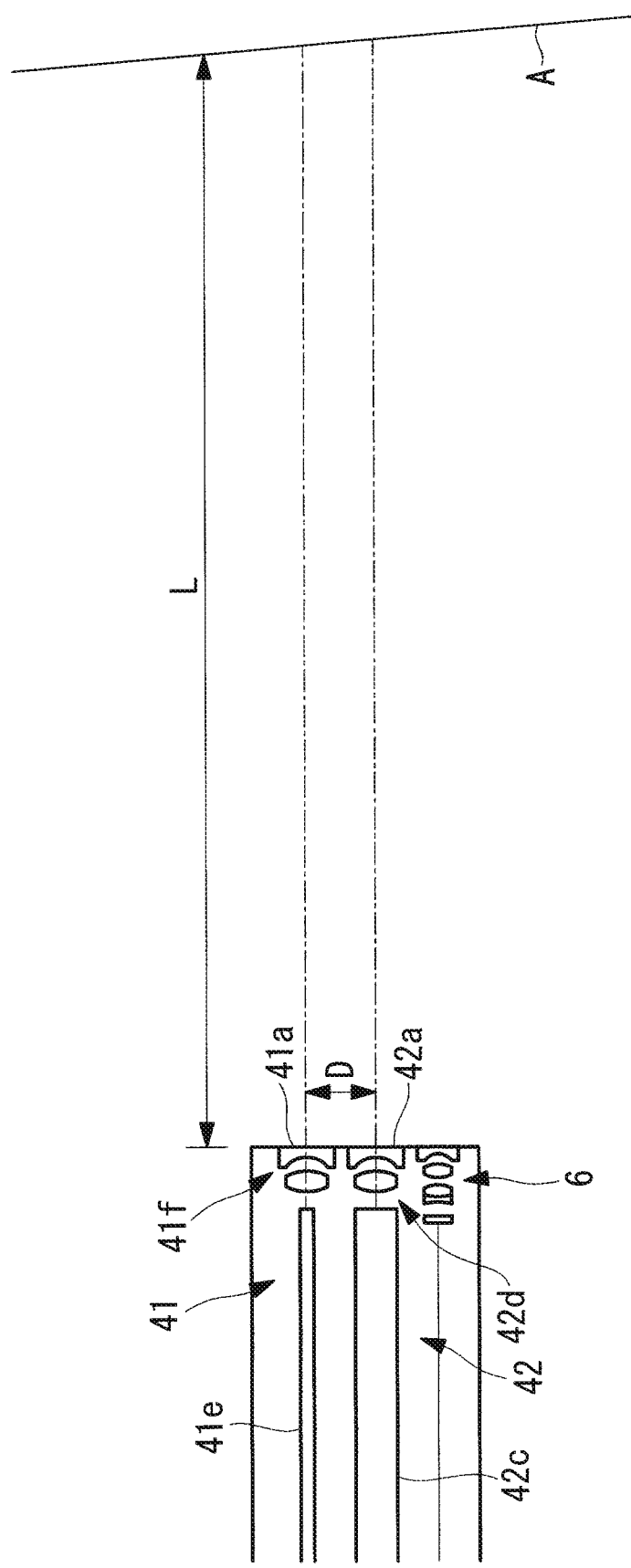
FIG. 13 is a diagram showing the relationship between: the distance D between the first and second exit faces; and the distance L from the first and second exit faces to biological tissue.

In this embodiment, it is desirable that Expression (1) below be satisfied. As shown in FIG. 13, in Expression (1), D is the distance (center-to-center distance) between the first exit face 41a and the second exit face 42a, and L is the distance from the first exit face 41a and the second exit face 42a (distal end face of the endoscope 2) to the biological tissue A. The distance L is set to a value within an appropriate range according to the focal distance of the endoscope 2.

$$D/L < 0.068 \tag{1}$$

Figure 14:
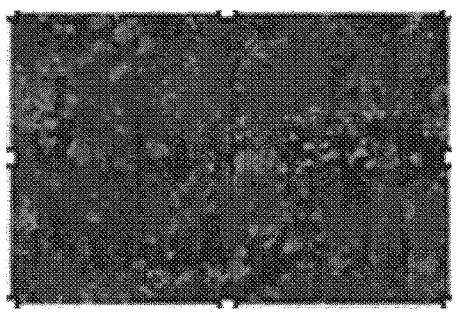
FIG. 14 is a diagram showing the relationships between D/L and noise in the surface-layer image and the deep-layer image and shows examples of the surface-layer image and the deep-layer image with different D/Ls.
Figure 14:
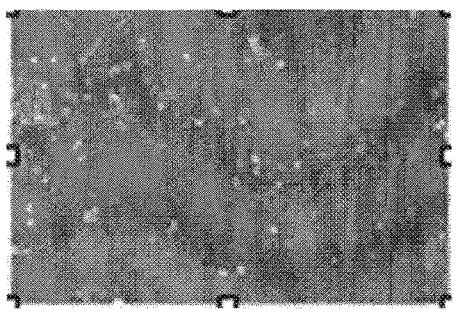
Figure 14:
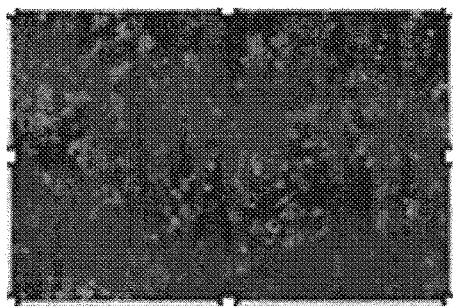
Figure 14:
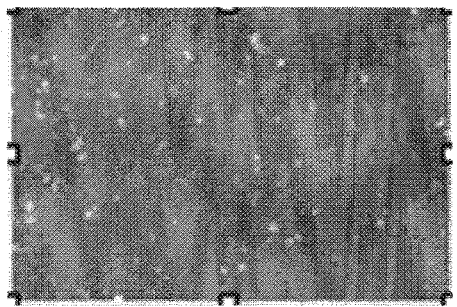
Figure 14:
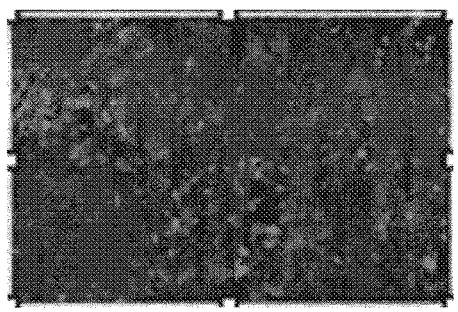
Figure 14:
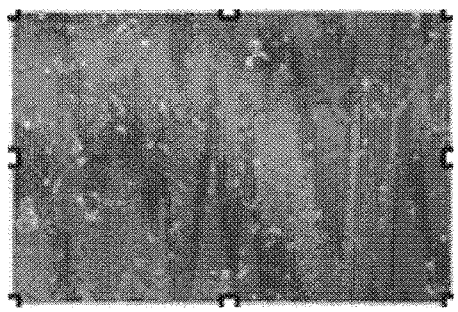
Figure 14:
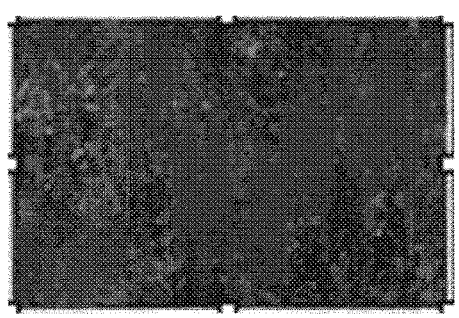
Figure 14:
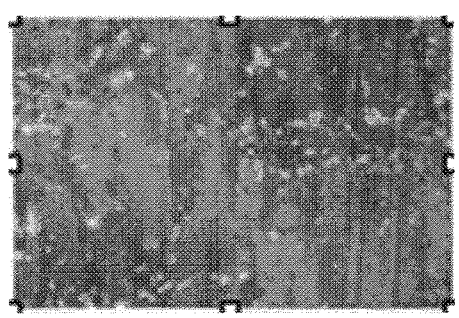
Figure 14:
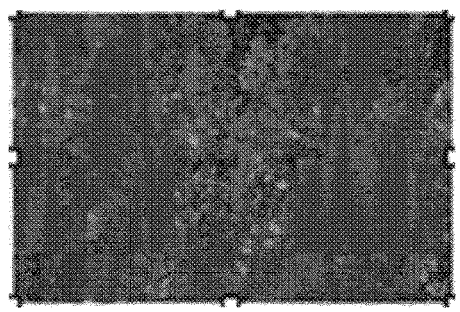
Figure 14:
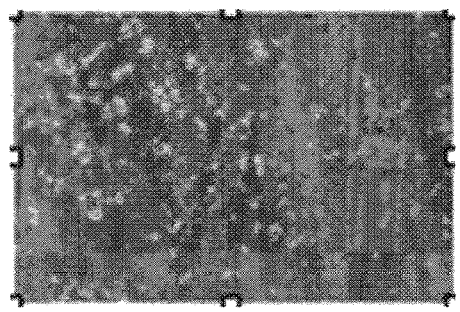

Due to the difference in position between the first exit face 41a and the second exit face 42a, the position of the specular light in the first illumination image and the position of the specular light in the second illumination image differ. When the first and second illumination images in which the positions of the specular light are different are used to generate a surface-layer image and a deep-layer image, white (i.e., high-gradation-value) spot-like noise occurs in the surface-layer image, and black (i.e., low-gradation-value) spot-like noise occurs in the deep-layer image. As shown in FIG. 14, the noise is more noticeable when the distance D between the exit faces 41a and 42a is larger or when the distance L from the exit faces 41a and 42a to the biological tissue A is smaller. FIG. 14 shows example surface-layer images and deep-layer images when D/L=0, 0.023, 0.045, 0.068, and 0.113.

Figure 15:
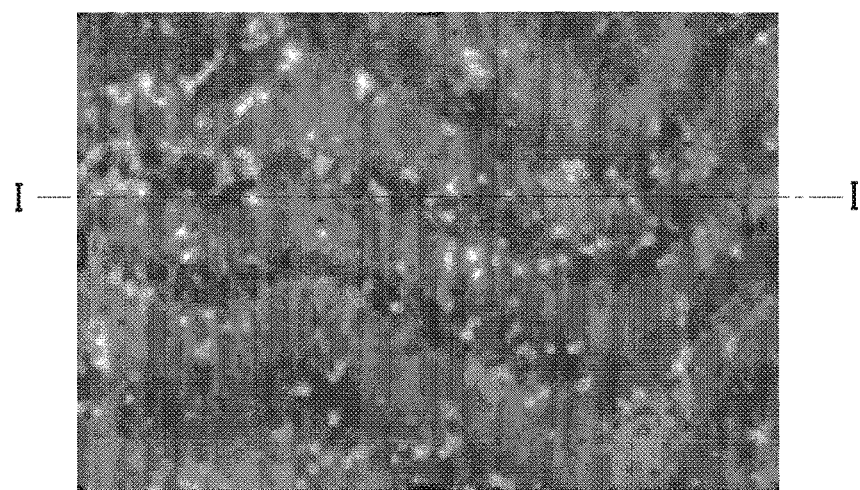
FIG. 15 is a deep-layer image with D/L=0.113.
Figure 16:
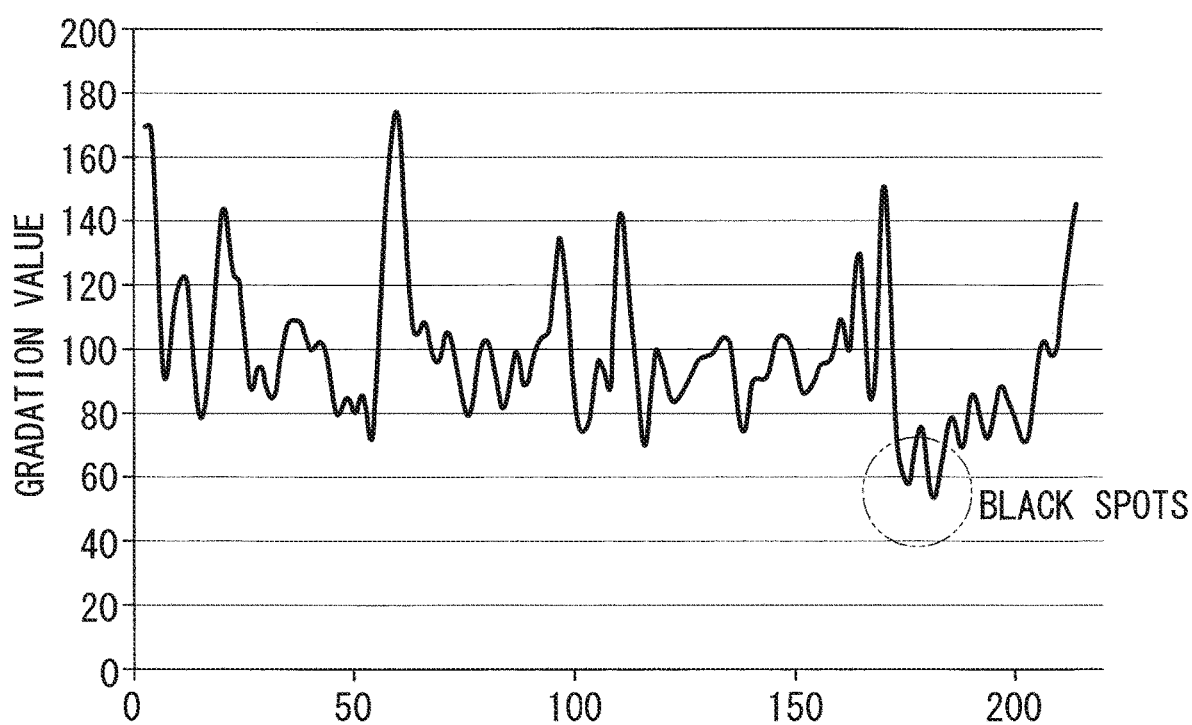
FIG. 16 is a gradation value profile taken along line I-I in FIG. 15.

FIG. 15 shows a deep-layer image when D/L=0.113, and FIG. 16 is a gradation value profile taken along line I-I in FIG. 15. As shown in FIG. 16, the gradation values of the black spots, which are noise, are less than or equal to 70.

Figure 17:
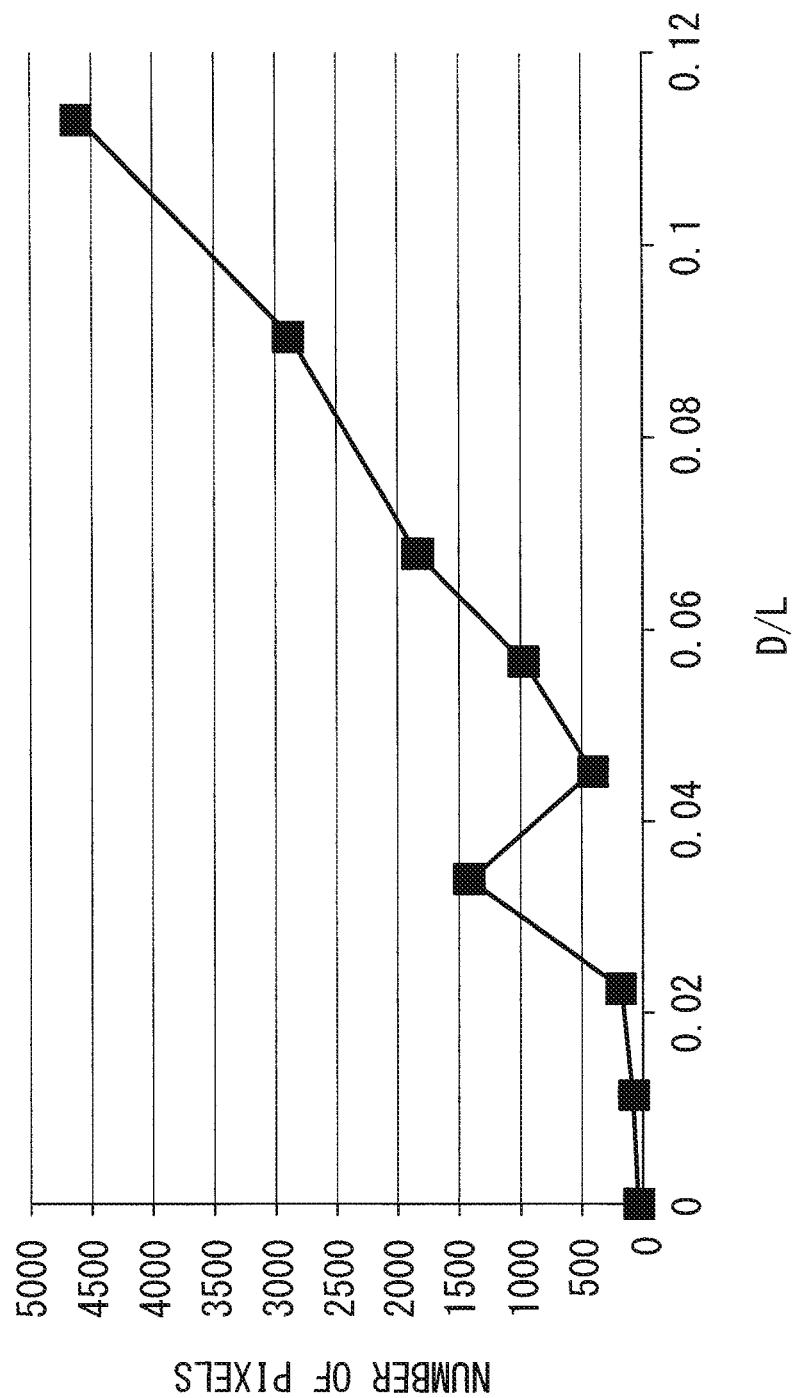
FIG. 17 is a graph showing the relationship between D/L and the number of pixels with a gradation value of less than or equal to 70.

FIG. 17 is a graph showing the relationship between the D/L value (horizontal axis) and the number of pixels having a gradation value of less than or equal to 70 in the deep-layer image (vertical axis). The graph shows that the number of pixels having a gradation value of less than or equal to 70, which represent black spots, tends to be small in the area satisfying D/L<0.068. This is because, when D/L<0.068 is satisfied, the position of the specular light in the first illumination image and the position of the specular light in the second illumination image substantially coincide. Accordingly, the black-spot noise in the deep-layer image can be prevented by satisfying Expression (1). For the same reason, the white-spot noise in the surface-layer image can be prevented by satisfying Expression (1).

As a result, the following aspect is read from the above described embodiment of the present invention.

An aspect of the present invention is an endoscope system including: a first illumination unit that emits, from a first exit face to a subject, first illumination light for imaging two sets of image information about the subject at different depths; a second illumination unit that emits, from a second exit face disposed at a different position from the first exit face to the subject, second illumination light having a wide band covering a visible band; an imaging unit that images a first illumination image of the subject illuminated with the first illumination light, and a second illumination image of the subject illuminated with the second illumination light; a separation processing unit that separates the two sets of image information from the first illumination image; and a separated-image generating unit that processes the second illumination image using the two sets of image information to generate two separated images each containing a large amount of information about the subject at the different depths.

According to this aspect, the second illumination image is imaged as a result of the imaging unit imaging an image of the subject illuminated with the second illumination light emitted from the second exit face. Meanwhile, the first illumination image is imaged as a result of the imaging unit imaging an image of the subject illuminated with the first illumination light emitted from the first exit face, and the separation processing unit separates two sets of image information at different depths contained in the first illumination image. By processing the second illumination image using the two sets of image information, it is possible to generate two separated images containing information about the subject at different depths.

In this case, because it is possible to brightly illuminate the subject with the second illumination unit, which is provided separately from the first illumination unit for imaging image information at different depths, it is possible to image a bright second illumination image. Based on this bright second illumination image, a bright separated image can be obtained.

In the above-described aspect, the first illumination light may have a spatially non-uniform intensity distribution including light portions and dark portions in a beam cross-section perpendicular to the optical axis.

When illumination light is radiated onto a subject that is a scatterer, specular reflection (specular) light specularly reflected at the surface of the subject, surface scattered light scattered in a surface layer inside the subject and emitted from the surface of the subject, and internal scattered light scattered in a deep layer inside the subject and emitted from the surface of the subject are produced. By radiating the first illumination light having a spatially non-uniform intensity distribution onto the subject, the internal scattered light is spatially separated from the specular light and the surface scattered light. Specifically, the specular light, the surface scattered light, and the internal scattered light are produced in the light portions, whereas the internal scattered light that spreads from the light portions to the dark portions is dominantly produced in the dark portions. Accordingly, it is possible to separate the image information at the deep layer from the areas corresponding to the dark portions in the first illumination image and to separate the image information at the surface and the surface layer from the areas corresponding to the light portions in the first illumination image.

In the above-described aspect, the light portions and the dark portions included in the first illumination light may be band-shaped, and the light portions and the dark portions may be alternately repeated in a width direction, forming a stripe shape.

This makes it possible to effectively separate the internal scattered light with a simple light/dark pattern. Furthermore, to switch the positions of the light portions and the dark portions of the stripe intensity distribution, it is only necessary to move the light portions and dark portions of the intensity distribution only in the width direction of the stripe. Hence, it is possible to easily change the intensity distribution of the illumination light with time.

In the above-described aspect, the light portions and the dark portions included in the first illumination light may have a substantially sine-wave-shaped intensity profile in the width direction.

By radiating such first illumination light having an intensity spatially changing in a sine-wave shape, it is possible to calculate, by using a phase shift method, the intensity value for a separated image of the surface layer when irradiated with the highest-intensity light and the intensity value for a separated image of the deep layer when irradiated with no light. Hence, it is possible to generate high-resolution good-quality separated images even from a small number of first illumination images.

In the above-described aspect, the shape of the wavelength spectrum of the first illumination light may be that of a single wavelength.

In the above-described aspect, the wavelength spectrum of the first illumination light and the wavelength spectrum of the second illumination light may have different shapes.

This makes it possible to image a first illumination image containing a larger amount of information at a specific depth in accordance with the shape of the wavelength spectrum of the first illumination light and thus to generate a separated image in which information at the specific depth is further emphasized.

In the above-described aspect, the first illumination light and the second illumination light may have different wavelength bands.

This makes it possible to image a first illumination image containing a larger amount of information at a specific depth corresponding to the wavelength band of the first illumination light and thus to generate a separated image in which information at the specific depth is further emphasized.

In the above-described aspect, the wavelength band of the first illumination light may be an infrared band.

In the above-described aspect, the first illumination unit and the second illumination unit may simultaneously emit the first illumination light and the second illumination light.

This makes it possible to obtain both the first illumination image and the second illumination image in a single imaging operation, thus improving the frame rate of the separated images.

In the above-described aspect, the distance D between the first exit face and the second exit face and the distance L from the first exit face and the second exit face to the subject may satisfy Expression (1) below:

$$D/L < 0.068 \tag{1}.$$

Due to the difference in position between the first exit face, through which the first illumination light is emitted, and the second exit face, through which the second illumination light is emitted, the position of the specular light in the first illumination image and the position of the specular light in the second illumination image differ, and, in the separated images formed from such first and second illumination images, white or black spot-like noise is generated. By satisfying Expression (1) above, the position of the specular light in the first illumination image and the position of the specular light in the second illumination image substantially coincide, thus preventing noise in the separated images.

In the above-described aspect, the separation processing unit may separate three or more sets of image information from two or more first illumination images imaged by radiating the first illumination light having dark portions with various widths, and the separated-image generating unit may generate three or more separated images using the three or more sets of image information.

By using a plurality of first illumination images of the subject illuminated with the first illumination light having the dark portions with various widths, it is possible to generate three or more separated images containing a large amount of information at different depths.

REFERENCE SIGNS LIST 1 endoscope system
2 endoscope
3 body part
41 first illumination unit
42 second illumination unit
5 intensity-distribution changing unit
6 imaging unit
7 image processing unit
71 separation processing unit
72 separated-image generating unit
L1 first illumination light
L2 second illumination light
A biological tissue
B surface
C surface layer
D deep layer

The invention claimed is:

1. An endoscope system comprising:
a first light source that is configured to emit, from a first exit face to a subject, first illumination light for imaging two sets of image information about the subject at different depths;
a second light source that is configured to emit, from a second exit face disposed at a different position from the first exit face to the subject, second illumination light having a wide band covering a visible band; and
a processor comprising hardware, the processor being configured to:
receive a first illumination image of the subject illuminated with the first illumination light and a second illumination image of the subject illuminated with the second illumination light;
separate the two sets of image information from the first illumination image; and
process the second illumination image using the two sets of image information to generate two separated images each containing a large amount of information about the subject at the different depths;
wherein the first illumination light has a spatially non-uniform intensity distribution including light portions and dark portions in a beam cross-section perpendicular to an optical axis,
a first set of the two sets of image information is a deep-layer component image that contains more information about a deep layer of the subject than a second set of the two sets, and the second set of the two sets of image information is a surface-layer component image that contains more information about a surface and a surface layer of the subject than the deep-layer component image, and
the processor is configured to:
generate a deep layer image in which information about the deep layer of the subject is emphasized over information about the surface and the surface layer of the subject by using and processing the deep-layer component image and the surface layer component image; and
generate a surface layer image in which information about the surface and the surface layer of the subject is emphasized over the deep layer image by using and processing the surface-layer component image and the deep layer component image.

2. The endoscope system according to claim 1, wherein the light portions and the dark portions included in the first illumination light are band-shaped, and
the light portions and the dark portions are alternately repeated in a width direction, forming a stripe shape.

3. The endoscope system according to claim 2, wherein the light portions and the dark portions included in the first illumination light have a substantially sine-wave-shaped intensity profile in the width direction.

4. The endoscope system according to claim 2, wherein the processor is configured to:
separate three or more sets of image information from two or more first illumination images imaged by radiating the first illumination light having dark portions with various widths, and
generate three or more separated images using the three or more sets of image information.

5. The endoscope system according to claim 1, wherein the shape of the wavelength spectrum of the first illumination light is that of a single wavelength.

6. The endoscope system according to claim 1, wherein the wavelength spectrum of the first illumination light and the wavelength spectrum of the second illumination light have different shapes.

7. The endoscope system according to claim 6, wherein the first illumination light and the second illumination light have different wavelength bands.

8. The endoscope system according to claim 1, wherein the wavelength band of the first illumination light is an infrared band.

9. The endoscope system according to claim 1, wherein the first light source and the second light source simultaneously emit the first illumination light and the second illumination light.

10. The endoscope system according to claim 1, wherein a distance D between the first exit face and the second exit face and a distance L from the first exit face and the second exit face to the subject satisfy Expression (1) below:

$$D/L < 0.068 \tag{1}$$

11. The endoscope system according to claim 1, wherein the processor generates the surface layer image on the basis of Expression (a) below and generates the deep layer image on the basis of Expression (b) below:

surface-layer image=second illumination image×surface-layer component image/(surface-layer component image+deep-layer component image) (a)

deep-layer image=second illumination image+deep-layer component image/(surface-layer component image+deep-layer component image) (b).

12. The endoscope system according to claim 1, wherein the processor generates the surface layer image on the basis of Expression (a) below and generates the deep layer image on the basis of Expression (b) below:

surface-layer image=second illumination image×$P$×surface-layer component image/(surface-layer component image+deep-layer component image) (a)

deep-layer image=second illumination image×$Q$×deep-layer component image/(surface-layer component image+deep-layer component image) (b)

where P and Q are coefficients.

* * * * *